(12) United States Patent
Howard et al.

(10) Patent No.: US 11,364,072 B2
(45) Date of Patent: Jun. 21, 2022

(54) CATHETER ELECTRODES FOR ENERGY MANAGEMENT

(71) Applicant: Medtronic, Inc., Minneapolis, MN (US)

(72) Inventors: Brian T. Howard, Bloomington, MN (US); Mark T. Stewart, Lino Lakes, MN (US); Damijan Miklavčič, Kranj (SL); Bushan K. Purushothaman, Plymouth, MN (US); Jeremy M. Stimack, Blaine, MN (US)

(73) Assignee: Medtronic, Inc., Minneapolis, MN (US)

(*) Notice: Subject to any disclaimer, the term of this patent is extended or adjusted under 35 U.S.C. 154(b) by 845 days.

(21) Appl. No.: 15/418,325

(22) Filed: Jan. 27, 2017

(65) Prior Publication Data

US 2018/0214202 A1  Aug. 2, 2018

(51) Int. Cl.
 *A61B 18/14* (2006.01)
 *A61B 5/287* (2021.01)
 (Continued)

(52) U.S. Cl.
 CPC .......... *A61B 18/1492* (2013.01); *A61B 5/287* (2021.01); *A61B 5/6852* (2013.01);
 (Continued)

(58) Field of Classification Search
 CPC . A61B 5/0422; A61B 5/6852; A61B 18/1492; A61B 34/20; A61B 2018/00577;
 (Continued)

(56) References Cited

U.S. PATENT DOCUMENTS 5,454,370 A * 10/1995 Avitall ................. A61B 5/0422
                                                  600/374
5,938,694 A *  8/1999 Jaraczewski ......... A61B 5/0422
                                                  607/122
(Continued)

FOREIGN PATENT DOCUMENTS

CN     104812297 A    7/2015
GB       2510452 A    8/2014

OTHER PUBLICATIONS

International Search Report and Written Opinion dated Apr. 25, 2018, for corresponding International Application No. PCT/US2018/015017; International Filing Date: Jan. 24, 2018 consisting of 13-pages.

(Continued)

*Primary Examiner* — Ronald Hupczey, Jr.
(74) *Attorney, Agent, or Firm* — Christopher & Weisberg, P.A.

(57) ABSTRACT

Methods, systems, and devices for enhancing the efficiency and efficacy of energy delivery and tissue mapping. One system includes a treatment element having a plurality of electrodes and an energy generator that is configured to deliver electric energy pulses to the electrodes in a variety of patterns. For example, electrodes may be arranged in closely spaced pairs. The energy generator may deliver mapping energy to each electrode in each pair individually to map tissue and may deliver ablation energy to the electrodes in each pair together, such that each pair is treated like a single electrode, to deliver ablation energy, such as bipolar ablation energy between adjacent pairs. One system includes at least one concave electrode, the configuration of which concentrates the energy and drives it deeper into the tissue. One system includes neutral electrodes between active elec- (Continued)

trodes, the energy generator selectively coupling the neutral electrodes to alter the ablation pattern.

11 Claims, 24 Drawing Sheets

(51) Int. Cl.
*A61B 34/20* (2016.01)
*A61B 5/00* (2006.01)
*A61B 18/00* (2006.01)

(52) U.S. Cl.
CPC .... *A61B 34/20* (2016.02); *A61B 2018/00577* (2013.01); *A61B 2018/00839* (2013.01); *A61B 2018/1407* (2013.01); *A61B 2018/1467* (2013.01); *A61B 2018/1475* (2013.01); *A61B 2034/2046* (2016.02)

(58) Field of Classification Search
CPC .. A61B 2018/00839; A61B 2018/1407; A61B 2018/1467; A61B 2018/1475; A61B 2034/2046
See application file for complete search history.

(56) References Cited

U.S. PATENT DOCUMENTS

| | | |
|---|---|---|
| 6,023,638 A | 2/2000 | Swanson |
| 2003/0028185 A1* | 2/2003 | He .......................... A61N 1/06 606/41 |
| 2005/0080409 A1 | 4/2005 | Young et al. |
| 2008/0281322 A1 | 11/2008 | Sherman et al. |
| 2013/0282085 A1* | 10/2013 | Lischinsky ............ A61B 18/14 607/102 |
| 2014/0052118 A1* | 2/2014 | Laske .................. A61B 5/6852 606/32 |
| 2014/0288546 A1* | 9/2014 | Sherman ............ A61B 18/1492 606/34 |
| 2016/0051322 A1* | 2/2016 | Asirvatham ....... A61B 18/1492 606/41 |
| 2016/0184004 A1* | 6/2016 | Hull .................... A61N 1/3625 600/509 |
| 2016/0287136 A1 | 10/2016 | Condie et al. |
| 2016/0331459 A1* | 11/2016 | Townley .................. A61N 7/00 |

OTHER PUBLICATIONS

China National Intellectual Property Administration, Notice on the First Office Action for corresponding CN Application No. 2018800087660, dated Feb. 18, 2022, 16 pages.

* cited by examiner

CATHETER ELECTRODES FOR ENERGY MANAGEMENT

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to methods, systems, and devices for enhancing the efficiency and efficacy of ablation energy delivery and tissue mapping. In particular, the present invention relates to improved electrodes, electrode configurations, and energy delivery patterns.

BACKGROUND

A cardiac arrhythmia is a condition in which the heart's normal rhythm is disrupted. Certain types of cardiac arrhythmias, including ventricular tachycardia and atrial fibrillation, may be treated by ablation (for example, radiofrequency (RF) ablation, pulsed RF ablation, pulsed electric field ablation, cryoablation, or the like). The success of an ablation procedure depends largely on the quality and sufficiency of the lesion(s) created during the procedure. For example, a lesion must be deep enough to destroy the arrhythmogenic tissue or adequately disrupt or isolate the aberrant electrical conduction within the myocardial tissue. Further, it may be desirable that the lesion(s) be continuous so a uniform ablation pattern is created over a larger area, rather than individual smaller lesions. Multi-electrode arrays facilitate the delivery of energy over a substantially continuous portion of tissue. In some situations, energy may be delivered between two or more electrodes in such an array to create continuous lesions (commonly referred to as bipolar ablation or bipolar mode).

Frequently, intracardiac electrogram mapping signals may be recorded from contact with the cardiac tissue by the electrodes of the ablation device, which may complicate the design of the treatment region of the device. For example, the electrodes must be close enough to each other that good-quality mapping signals are recorded from the tissue and the local activation and far-field depolarizations may be distinguished. However, the required spacing for mapping is too small to be ideal for the bipolar ablation techniques.

SUMMARY

The present invention advantageously provides methods, systems, and devices for enhancing the efficiency and efficacy of ablation energy delivery and tissue depolarization and voltage mapping. In one embodiment, a system for the delivery of ablation energy may include a medical device configured to ablate and map tissue, the medical device including a treatment element having a plurality of electrodes, the electrodes being arranged in a plurality of pairs of a first electrode and a second electrode, the first electrode and the second electrode of each electrode pair being separated by a first distance, each electrode pair being separated by a second distance greater than the first distance; and an energy generator in communication with the treatment element, the energy generator being configured to: electrically connect each of the plurality of electrodes to the energy generator; electrically connect the first electrode and the second electrode of each of the plurality of electrode pairs to each other such that every other electrode pair has the same polarity; and transmit ablation energy to the plurality of electrodes such that energy is delivered between electrode pairs.

In one aspect of this embodiment, the first distance may be between approximately 1.0 mm and approximately 2.0 mm. In one aspect of this embodiment, the second distance may be between approximately 2.0 mm and 6.0 mm.

In one aspect of this embodiment, the system may further include a mapping intracardiac electrogram (EGM) signal recording system and a navigation system, the energy generator being further configured to, when the energy generator is not transmitting ablation energy: electrically disconnect the first electrode and the second electrode of each of the plurality of electrode pairs from each other; connect each of the plurality of electrodes to the EGM signal recording system and the navigation system; and at least one of transmit navigation energy to and receive navigation energy from each of the plurality of electrodes while allowing the signal recording system to record intracardiac electrogram signals from each of the electrode pair; and when using electric potential based navigation systems, at least one of transmit and receive navigation energy through each of the plurality of electrodes while allowing the mapping signal recording system to record intracardiac electrogram signals from each of the plurality of electrodes.

In one aspect of this embodiment, the system may further include a cardiac signal recording system and a positioning and navigation system, the energy generator being further configured to, when the energy generator is not transmitting ablation energy: electrically disconnect the first electrode and the second electrode of each of the plurality of electrode pairs from each other; connect each of the plurality of electrodes to the cardiac signal recording system and to the positioning and navigation system; transmit cardiac electrical activity measurements to the cardiac signal recording system; and transmit positioning and navigation signals to or from each of the plurality of electrodes.

In one aspect of this embodiment, the plurality of electrodes may be a first plurality of electrodes, the treatment element further having a second plurality of electrodes, each electrode of the second plurality of electrodes being located between adjacent electrode pairs of the first plurality of electrodes. In one aspect of this embodiment, the second plurality of electrodes may be electrically disconnected from the energy generator and the mapping signal recording system when the energy generator transmits ablation energy.

In one aspect of this embodiment, the treatment element further may have a carrier element, each of the plurality of electrodes being located on the carrier element. In one aspect of this embodiment, the treatment element may have an expanded configuration in which the carrier element has a substantially circular shape or the carrier may have a substantially linear shape.

In one embodiment, a system for the delivery of ablation energy may include: a medical device including a treatment element having a plurality of electrodes, the electrodes being arranged in a plurality of sets of a first electrode, a second electrode, and a third electrode; and an energy generator in communication with the treatment element, the energy generator being configured to: electrically connect the first electrode and the second electrode of each electrode set to each other; electrically connect the first electrode and the second electrode of every other electrode set to a first polarity of the energy generator; electrically connect the first electrode and the second electrode of each of a plurality of remaining electrode sets to a second polarity of the energy generator; electrically disconnect the third electrode of each electrode set from the energy generator; and transmit ablation energy to the plurality of electrodes such that adjacent electrode sets deliver bipolar energy therebetween, thus allowing an effectively wider electrode spacing and effectively larger electrode areas when delivering energy.

In one aspect of this embodiment, the energy generator further may be configured to: electrically connect the second electrode and the third electrode of each electrode set to each other; electrically connect the second electrode and the third electrode of every other electrode set to a first polarity of the energy generator; electrically connect the second electrode and the third electrode of each of a plurality of remaining electrode sets to a second polarity of the energy generator; electrically disconnect the first electrode of each electrode set from the energy generator; and transmit ablation energy to the plurality of electrodes such that adjacent electrode sets deliver bipolar energy therebetween.

In one embodiment, a device for the delivery of ablation energy may include an elongate body including a distal portion and a proximal portion, and a treatment element at the distal portion of the elongate body, the treatment element including at least one concave electrode, the at least one concave electrode having at least one of a concave cylindrical configuration and a hemispherical configuration.

In one aspect of this embodiment, the treatment element may have a linear configuration, the at least one concave electrode being a plurality of concave electrodes, each of the plurality of concave electrodes having a concave cylindrical configuration.

In one aspect of this embodiment, the at least one concave electrode may include a concave distal tip electrode having a hemispherical configuration, the elongate body further including a distalmost tip and the treatment element having a linear configuration. In one aspect of this embodiment, the concave distal tip electrode may be recessed within the elongate body a distance from the distalmost tip of the elongate body.

In one aspect of this embodiment, the at least one concave electrode may include a plurality of concave electrodes each having a concave cylindrical configuration, the treatment element including a flexible carrier element bearing the plurality of concave electrodes.

In one embodiment, a device for the delivery of ablation energy may include an elongate body including a distal portion and a proximal portion, and a treatment element at the distal portion of the elongate body, the treatment element including at least one electrode and at least one insulated circumferential protuberant segment, the at least one insulated circumferential protuberant segment being between immediately adjacent to the at least one electrode, the at least one insulated circumferential protuberant segment having at least one circumferential protrusion with a diameter that is greater than a greatest diameter of the at least one electrode.

In one aspect of this embodiment, the treatment element further may include a carrier element, each of the at least one electrode and the at least one insulated protuberant segment being on the carrier element, the greatest diameter of the at least one electrode being greater than a diameter of the carrier element.

In one aspect of this embodiment, the at least one insulated circumferential protuberant segment may have a first end and a second end, the at least one insulated circumferential protuberant segment having a first protrusion at the first end having a first diameter and a second protrusion at the second end having the first diameter, and a length therebetween having a second diameter, the first diameter being greater than the second diameter.

In one aspect of this embodiment, the treatment element may include an insulated carrier element, the insulated carrier element defining the at least one insulated circumferential protuberant segment.

In one embodiment, a system for the delivery of ablation energy may include: a treatment element including at least two active electrodes and at least two neutral electrodes, two of the at least two neutral electrodes being between two of the at least two active electrodes; and an energy generator in communication with the treatment element, the energy generator being configured to: deliver ablation energy to the at least two active electrodes; and selectively electrically couple and decouple the at least two neutral electrodes from each other during the delivery of ablation energy to the at least two active electrodes.

In one embodiment, a system for the delivery of ablation energy may include: an energy generator having a first polarity and a second polarity; and a treatment element including: at least one active electrode in electrical communication with one of the first polarity and the second polarity; and a plurality of active electrodes in electrical communication with an other of the first polarity and the second polarity.

In one aspect of this embodiment, the at least one active electrode may include one active electrode. In one aspect of this embodiment, the plurality of active electrodes may include at least eight electrodes.

In one embodiment, a system for the delivery of ablation energy may include: a first medical device including a treatment element having a plurality of electrodes, the plurality of electrodes having a first at least one electrode and a second at least one electrode, the first and second at least one electrode being different, the second at least one electrode including a greater number of the plurality of electrodes than the first at least one electrode; a second medical device including a ground electrode; and an energy generator in communication with the treatment element, the energy generator being configured to selectively: deliver bipolar energy through the plurality of electrodes; and deliver unipolar energy through the plurality of electrodes and the ground electrode. The energy generator is further configured to deliver energy having a first polarity through the first at least one electrode and to deliver energy having a second polarity through the second at least one electrode such that a greater amount of energy is delivered through the first at least one electrode than the second at least one electrode.

In one aspect of this embodiment, the plurality of electrodes may include a third at least one electrode that is electrically disconnected from the energy generator.

In one aspect of this embodiment, the plurality of electrodes may include nine electrodes, the first plurality of electrodes including two electrodes and the second plurality of electrodes including five electrodes.

In one aspect of this embodiment, the treatment element may include a carrier element having an at least substantially circular shape, the plurality of electrodes being radially distributed on the carrier element, the first at least one electrode being at a first position on the carrier element and the second at least one electrode being at a second location on the carrier element that is approximately 180° from the first location. In one aspect of this embodiment, the first at least one electrode and the second at least one electrode include the same number of electrodes.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
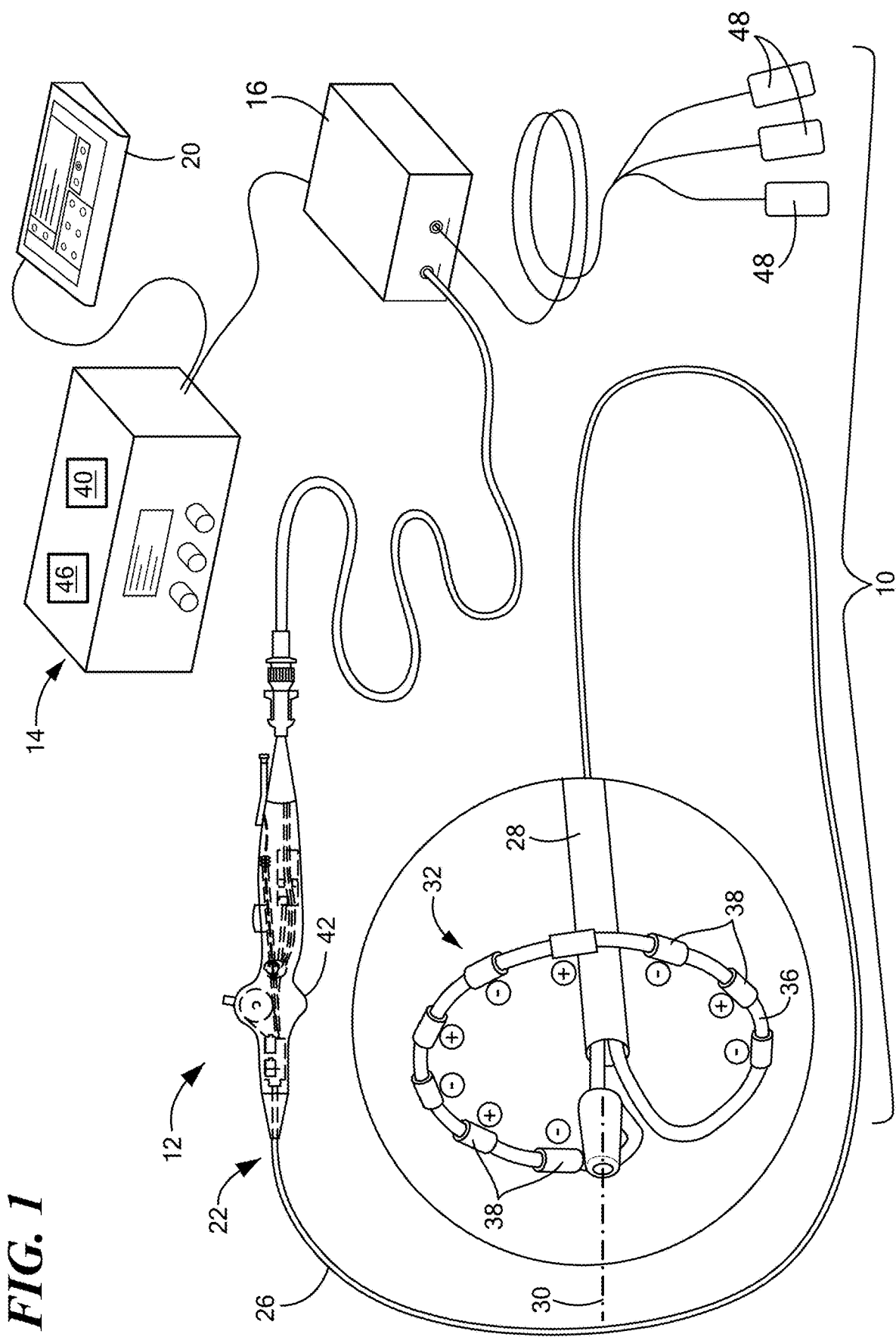
FIG. 1 shows a first exemplary system including a medical device for recording high-fidelity EGM recordings as well as delivering pulsed electric field ablation energy.

The devices and systems disclosed herein increase the efficacy of treatment procedures by enhancing lesion formation and depth and improve mapping signal quality.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein. For simplicity, electric fields may not be shown to actual scale or orientation in order to simply depict the relative polarities of monophasic or biphasic pulsed voltages or currents.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. The terms "active" or "powered" may be used to indicate electrodes that are connected to either the positive or negative polarity of the electrical energy source, thereby producing an electric current between such powered but opposite polarity electrodes. In a similar manner, electrodes termed as "neutral," "inactive," "disconnected," "decoupled," or "unpowered" are those electrodes that are not connected to either of the polarities of the source of electrical energy during such energy deliveries. In a similar manner, during energy deliveries from active electrodes, the active electrodes as well as inactive mapping electrodes may be disconnected from the mapping system during the period of energy delivery and reconnected to the electrogram mapping system upon cessation of energy delivery. Additionally, following a set of deliveries of energy between active electrode pairs, the roles of active and neutral electrodes may be reversed such that the active pairs become neutral and the formerly neutral electrodes become the active electrodes, thus substantially altering the electric field vectoring between the first and second sets of energy deliveries. One having ordinary skill in the art will appreciate that multiple components may interoperate and modifications and variations are possible of achieving the electrical and data communication.

Referring now to the drawing figures in which like reference designations refer to like elements, a first exemplary embodiment of a medical system constructed in accordance with the principles of the present invention is shown in FIG. 1, generally designated as "10." The system 10 may generally include a medical device 12, such as a catheter, that may be coupled directly to an energy supply, such as a pulsed electric field or radiofrequency (RF) generator 14 including an energy control, delivering, and monitoring system or indirectly through a device electrode distribution system 16 (which may also be referred to herein as a catheter electrode distribution system or CEDS). The system 10 may also include a remote controller 20 that is in communication with the generator 14 for operating and controlling the various functions of the generator 14. Further, the medical device 12 may include one or more diagnostic or treatment regions for the energetic, therapeutic, and/or investigatory interaction between the medical device 12 and a treatment site. As a non-limiting example, the treatment region(s) may deliver pulsed electric field electroporation energy and/or radiofrequency energy to a tissue area in proximity to the treatment region(s).

The medical device 12 may serve both as a treatment device and a mapping device. The medical device 12 may include an elongate body 22 passable through a patient's vasculature and/or proximate to a tissue region for diagnosis or treatment. For example, the device 12 may be a catheter that is deliverable to the tissue region via a sheath or intravascular introducer (not shown). The elongate body 22 may define a proximal portion 26, a distal portion 28, and a longitudinal axis 30, and may further include one or more lumens disposed within the elongate body 22 thereby providing mechanical, electrical, and/or fluid communication between the elongate body proximal portion 26 and the elongate distal portion 28.

The medical device 12 may further include one or more treatment elements 32 at, coupled to, or on the elongate body distal portion 28 for energetic, therapeutic, and/or investigatory interaction between the medical device 12 and a treatment site or region. As a non-limiting example, the device 12 may include a treatment element 32, such as that shown in FIGS. 1-12, that includes a carrier element 36 bearing a plurality of electrodes 38. The carrier element 36 may be transitionable between a linear configuration and an expanded configuration in which the carrier element 36 has an arcuate or substantially circular configuration. For example, the carrier element 36 may form a loop in the expanded configuration, which may lie in a plane that is substantially orthogonal to the elongate body longitudinal axis 30. The planar orientation of the expanded carrier element 36 may facilitate placement of the plurality of electrodes 38 in contact with the tissue at the treatment site. Alternatively, the medical device 12 may have a substantially linear configuration with the plurality of electrodes 38 located in a common longitudinal axis along the length of at least a portion of the elongate body distal portion 28 (for example, a focal catheter).

The plurality of electrodes 38 may also perform diagnostic functions, such as collection of intracardiac electrograms (EGM) and/or monophasic action potentials (MAPs) as well as performing selective pacing of intracardiac sites for diagnostic purposes. Measured signals may be transferred from the device electrode energy distribution system 16 to a recording system input box 40, which may be included in or integrated with the generator 14. The plurality of electrodes 38 may also monitor the proximity to target tissues and quality of contact with such tissues using impedance based measurements with connections to the device electrode energy distribution system 16. The device electrode energy distribution system 16 may include high speed relays to disconnect/reconnected specific electrodes 38 from the generator 14 during an energy delivery procedure. Immediately following the pulsed energy deliveries, the relays may reconnect the electrode(s) 38 so they may be used for diagnostic purposes.

Although not shown, the system 10 may include one or more sensors to monitor the operating parameters throughout the system, in addition to monitoring, recording or otherwise conveying measurements or conditions within the medical device 12 or the ambient environment at the distal portion of the medical device 12. The sensor(s) may be in communication with the generator 14 and/or the electrode distribution system 16 for initiating or triggering one or more alerts or therapeutic delivery modifications during operation of the medical device 12.

The medical device 12 may include a handle 42 coupled to the elongate body proximal portion 26. The handle 42 may include circuitry for identification and/or use in controlling of the medical device 12 or another component of the system. Additionally, the handle 42 may also include connectors that are mateable to the generator 14 and/or the electrode distribution system 16 to establish communication between the medical device 12 the generator 14 and/or the electrode distribution system 16. The handle 42 may also include one or more actuation or control features that allow a user to control, deflect, steer, or otherwise manipulate a distal portion of the medical device 12 from the proximal portion of the medical device 12.

Electroporation is a phenomenon causing cell membranes to become "leaky" (that is, permeable for molecules for which the cell membrane may otherwise be impermeable or semipermeable). Electroporation, which may also be referred to as electropermeabilization, pulsed electric field treatment, non-thermal irreversible electroporation, irreversible electroporation, high frequency irreversible electroporation, nanosecond electroporation, or nanoelectroporation, involves the application of high-amplitude pulses to cause physiological modification (i.e., permeabilization) of the cells of the tissue to which the energy is applied. These pulses preferably may be short (for example, nanosecond, microsecond, or millisecond pulse width) in order to allow the application of high voltage, high current (for example, 20 or more amps) without long duration(s) of electrical current flow that may cause significant tissue heating and muscle stimulation. The pulsed electric energy may induce the formation of microscopic defects that result in hyperpermeabilization of the cell membrane. Depending on the characteristics of the electrical pulses, an electroporated cell can survive electroporation, referred to as "reversible electroporation," or die, referred to as "irreversible electroporation" (IEP). Reversible electroporation may be used to transfer agents, including genetic material and other large or small molecules, into targeted cells for various purposes, including the alteration of the action potentials of cardiac myocytes.

As such, the generator 14 may include processing circuitry including a processor 46 in communication with one or more controllers and/or memories containing software modules containing instructions or algorithms to provide for the automated operation and performance of the features, sequences, calculations, or procedures described herein and/or required for a given medical procedure. The system 10 may further include a plurality of surface ECG electrodes 48 in communication with the generator 14 through the device electrode distribution system 16. The plurality of surface ECG electrodes 48 may be part of a positioning and navigation system 49 that allows for the localization of the electrodes within three-dimensional space within the patient's body through the transmission and receipt of positioning and navigation signals to and from the generator 14. When the surface electrodes 48 are applied to the skin of a patient, they may be used, for example, to monitor the patient's cardiac activity to determine pulse train delivery timing at the desired portion of the cardiac cycle (that is, to record and transmit electrical activity measurements to the generator 14) and/or for navigation and location of the device 12 within the patient. In addition to monitoring, recording, or otherwise conveying measurements or conditions within the medical device 12 or the ambient environment at the distal portion 28 of the medical device 12, additional measurements may be made through connections to the multi-electrode device, such as temperature, electrode-tissue interface impedance, delivered charge, current, power, voltage, work, or the like in the generator 14 and/or the device 12. The surface ECG electrodes 48 may be in communication with the generator 14 for determining the timing during a cardiac cycle at which to initiate or trigger one or more alerts or therapeutic deliveries during operation of the medical device 12. Additional neutral electrode patient ground patches (not shown) may be used to evaluate the desired bipolar electrical path impedance, as well as monitor and alert the operator upon detection of undesired and/or unsafe conditions. As used herein, the term "bipolar ablation" or "bipolar energy" may refer to the delivery of electric pulses between two device electrodes, rather than between a single device electrode and a ground electrode (for example, as is the case in unipolar ablation). The generator 14 may be configured to deliver a sampling pulse prior to delivery of a full series or "pulse train" of pulsed electric field ablative therapy pulses. Such a preliminary sampling pulse may provide measurements of relative electrical impedance between electrodes and warning of inappropriate electrode configurations such as overlapping electrodes that could result in, for example, a short circuit condition. Additionally, such preliminary pulses may be used to evaluate such conditions as relative proximity of individual electrodes to ensure an appropriate voltage is to be applied to the electrodes during subsequent energy delivery. These preliminary pulses may also be applied to assess whether the electrodes in positioned properly relative to the target tissue. The preliminary pulses may be delivered with or without automated, immediate, subsequent delivery of one or more therapeutic pulse trains.

The generator 14 may provide electrical pulses to the medical device 12 to perform an electroporation procedure to cardiac tissue or other tissues within the patient's body, such as renal tissue, airway tissue, and organs or tissue within the cardiac space. Specifically, generator 14 may be configured and programmed to deliver pulsed, high-voltage electric fields appropriate for achieving desired pulsed, high-voltage ablation (referred to as "pulsed field ablation" or "pulsed electric field ablation") and/or pulsed radiofrequency ablation. As a point of reference, the non-radiofrequency pulsed high-voltage ablation effects of the present disclosure are distinguishable from DC current ablation, as well as thermally-induced ablation attendant with conventional RF techniques. For example, the pulse trains delivered by generator 14 may be delivered at a frequency less than 30 kHz, and in an exemplary configuration, 1 kHz, which is a lower frequency than radiofrequency treatments. The pulsed-field energy in accordance with the present disclosure may be sufficient to induce cell death for purposes of completely blocking an aberrant conductive pathway along or through cardiac tissue, destroying the ability of the so-ablated cardiac tissue to propagate or conduct cardiac depolarization waveforms and associated electrical signals. Additionally or alternatively, the generator 14 may be configured and programmed to deliver RF energy appropriate for achieving tissue ablation.

Figure 2:
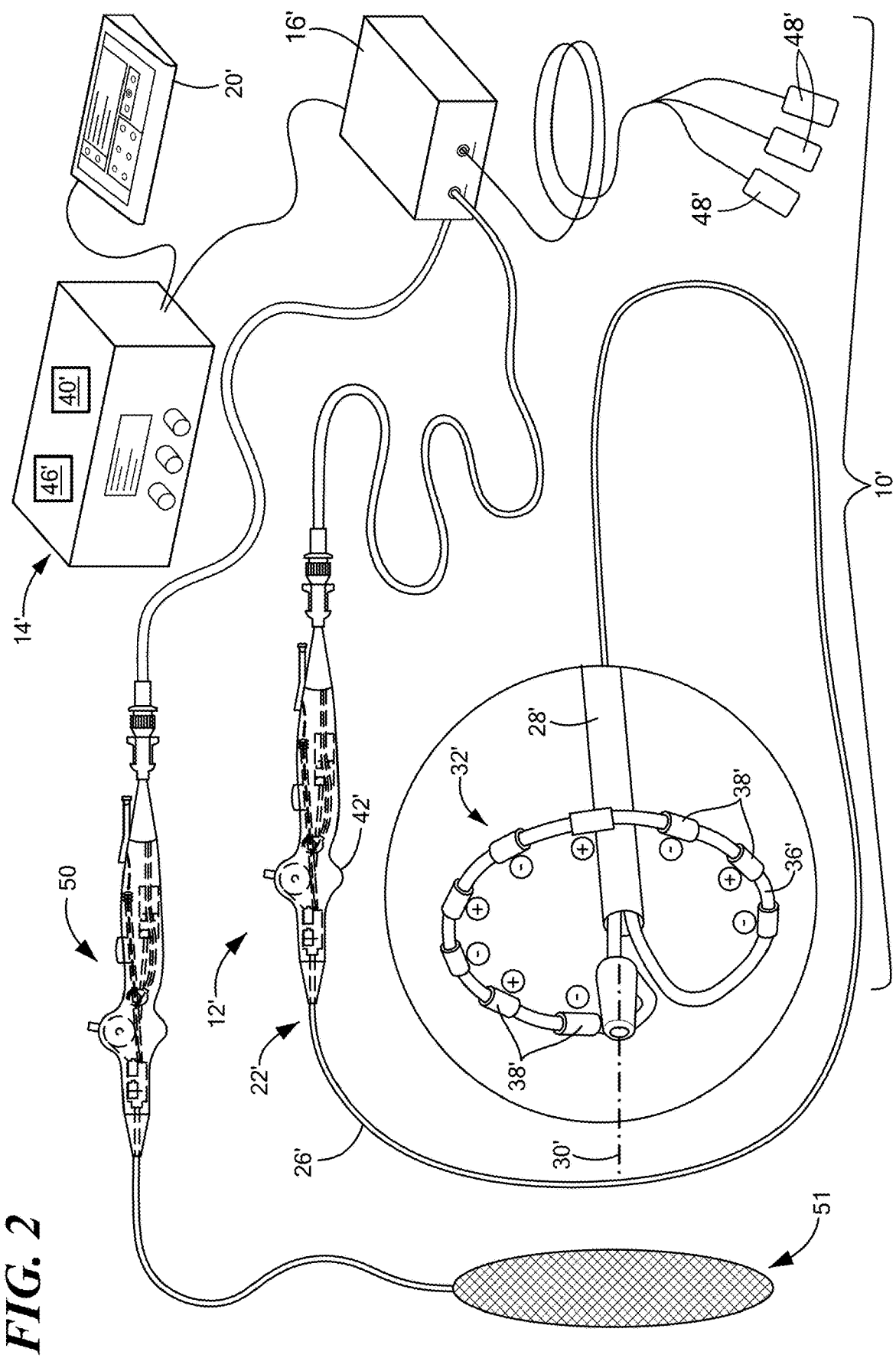
FIG. 2 shows a second exemplary system including a first medical device for recording high-fidelity EGM recordings as well as delivering pulsed electric field ablation energy and a second medical device for providing an alternative electrical delivery pathway.

Referring to FIG. 2, a second exemplary embodiment of a medical system is shown. The components of the system 10' shown in FIG. 2 may be the same or at least substantially the same as the components shown and described in the system 10 of FIG. 1 (as is indicated by the use of the primed corresponding reference numbers). However, the system shown in FIG. 2 may additionally include a second medical device 50 in communication with the device electrode distribution system 16' and the generator 14'. The second medical device 50 may be used to provide an alternative electrical vector (that is, delivery) pathway in addition to the purely bipolar vectors used between specific pairs of electrodes on the same array. The second medical device 50 may include an element 51 that functions as a return electrode. Accordingly the element 51 may have a relatively large surface area (for example, a surface area that is larger than that of a treatment electrode 38' of the treatment element 32' of the first medical device 12') suitable for use as an indwelling return current path. The element 51 may be positioned proximate the treatment element 32', for example, within the pulmonary artery, the vena cavae, aorta, pericardial space, esophagus, or other indwelling location. During the delivery of pulsed electric field energy, a series of different bipolar energy vectors may be used between selected electrodes 38' of the treatment element 32', followed by or preceded by energy delivery between a plurality of electrodes 38' and the indwelling element 51 of the second medical device 50. Energy delivery between the plurality of electrodes 38' and the element 51 is considered to be unipolar energy delivery because the electrode area of the second medical device 50 (the element 51) is greater than the electrode area of the first medical device 12' (electrodes 38'). The ablative effect may be controlled through the positioning of the second medical device and element 51. For example, the indwelling element 51 of the second medical device 50 may be positioned within the right or left ventricular outflow tracts, such as within the pulmonary arterial system or within the aorta. Additionally or alternatively, the element 51 may be positioned within the coronary sinus or great coronary vein of the heart. Field vectors from such locations may promote the creation of transmural lesions through the left atrial wall in such areas. Further, delivery of energy in this unipolar mode may be combined with delivery of energy in bipolar mode (that is, between the electrodes 38' of the first medical device 12'). Such a system may be used for any of the delivery patterns discussed herein, adding the option of also delivering energy in unipolar mode using the return electrode element 51.

Referring to FIGS. 3-25, embodiments of a distal portion 28 of a medical device including a treatment element 32 and energy delivery patterns are shown. As discussed below, some of the delivery patterns are delivered in sequence during a treatment and are not necessarily standalone delivery patterns. The energy fields shown in FIGS. 3-25 (that is, the concentric circles surrounding the electrodes 38) are meant for illustration only, and do not necessarily accurately represent the size and configuration of the actual energy field delivered by the electrodes 38. Further, the delivery patterns discussed herein are not necessarily mutually exclusive, and may be combined during an ablation procedure.

Figure 3:
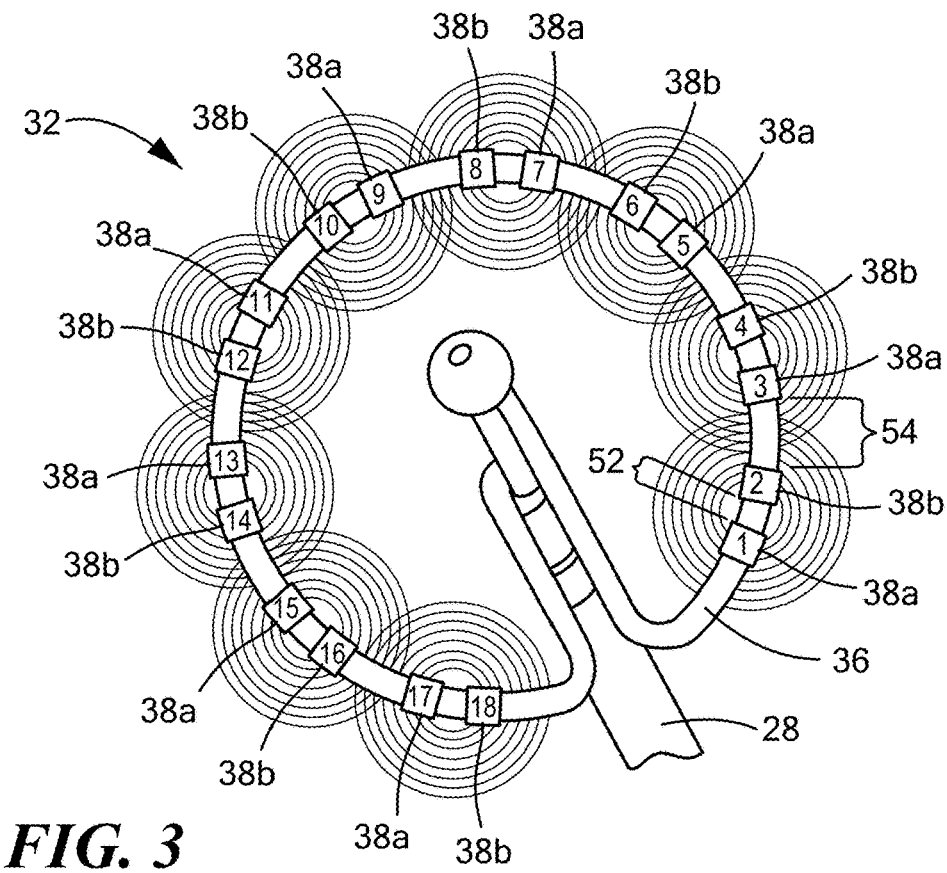
FIG. 3 shows a distal portion of the medical device having a first configuration of electrodes, the electrodes delivering ablation energy in a first delivery pattern.

Referring now to FIG. 3, a treatment element 32 having a first configuration of electrodes 38 is shown. The treatment element 32 may include a carrier element 36 bearing a plurality of electrodes 38. Although the term "plurality" is used to refer to different groups of electrodes of the plurality of electrodes 38, it will be understood that a single electrode 38 may have the characteristics described for a particular group of electrodes. That is, for simplicity, a single electrode may be referred to as a "plurality of electrodes" for purposes of comparison to a different plurality of electrodes. Thus, a plurality of electrodes as referred to herein may include at least one electrode. For example, a treatment element 32 including a plurality of electrodes 38 may include a first at least one electrode 38a and a second at least one electrode 38b.

As a non-limiting example, eighteen electrodes are shown in FIG. 3 with consecutive electrode numbering shown on each electrode (labeled with numbers 1-18, referred to herein as electrodes E1-E18). Each electrode 38 may be composed of an electrically conductive material, such as a metal. Each electrode 38 may be relatively small, between approximately 1.0 mm and approximately 2.0 mm in length, and may have a diameter that is larger than the diameter of the carrier element 36, such that the electrodes 38 protrude from the carrier element 36. This size difference may cause the electrode(s) 38 to push into the tissue with which they are in contact, which may enhance mapping signal (for example, EGM and/or MAP) quality. Further, the electrodes 38 may be arranged on the carrier element 36 in closely spaced pairs. In FIG. 3, there are nine pairs of electrodes and each pair includes electrodes 38a and 38b. For example, the space 52 between the electrodes 38a, 38b of each pair may be between approximately 1.0 mm and approximately 2.0 mm. The space 54 between adjacent pairs of electrodes 38a, 38b may be larger, for example, between approximately 2.0 mm and approximately 6.0 mm. The electrode configuration may provide high-fidelity EGM recordings from the closely spaced pairs 38a, 38b. It will be understood that the treatment element 32 may include a first electrode (for example, E1 in FIG. 3) and a last electrode (for example, E18 in FIG. 3), and the spacing discussed herein may apply to electrodes from the first electrode to the last electrode. In other words, the first electrode may be spaced from the last electrode by a distance that is different than the exemplary distances provided herein.

Although other energy modalities may be used, the delivery of pulsed electric field energy will be discussed in reference to FIGS. 3-13. When pulsed electric field ablation energy is delivered, it may be delivered in a manner that treats each closely spaced electrode pair 38a, 38b as a single electrode. In other words, the two electrodes 38a, 38b of each pair may be electrically connected to each other. Energy delivery using this configuration may approximate energy delivery from devices with currently known electrode configurations, such as those that include larger electrodes (for example, 3.0 mm electrodes) with larger spacing (for example, 3.75 mm). However, the configuration shown in FIG. 3 may provide higher quality EGM recordings than currently used electrode configurations with larger electrodes and larger spacing of greater than 3.0 mm.

The device electrode distribution system 16 may allow bipolar EGM recording from the closely spaced electrode pairs by connecting each electrode 38 to the recording system 40 independently when ablation energy is not being delivered. To deliver ablation energy, the device electrode energy distribution system 16 electrically connects the electrode pair 38a, 38b to treat the pair as a single electrode. Thus, the electrodes 38 may be used to both deliver ablation energy and to record mapping signals. This configuration allows relatively high applied voltages to be applied to electrode pairs that are separated from adjacent pairs by an adequate distance to produce the desired electric field strength distribution and uniform ablation. For example, the larger spacing 54 between electrode pairs 38a, 38b may provide adequate separation when adjacent or neighboring pairs are energized with opposite polarities, as is the case in a bipolar ablation.

Figure 4:
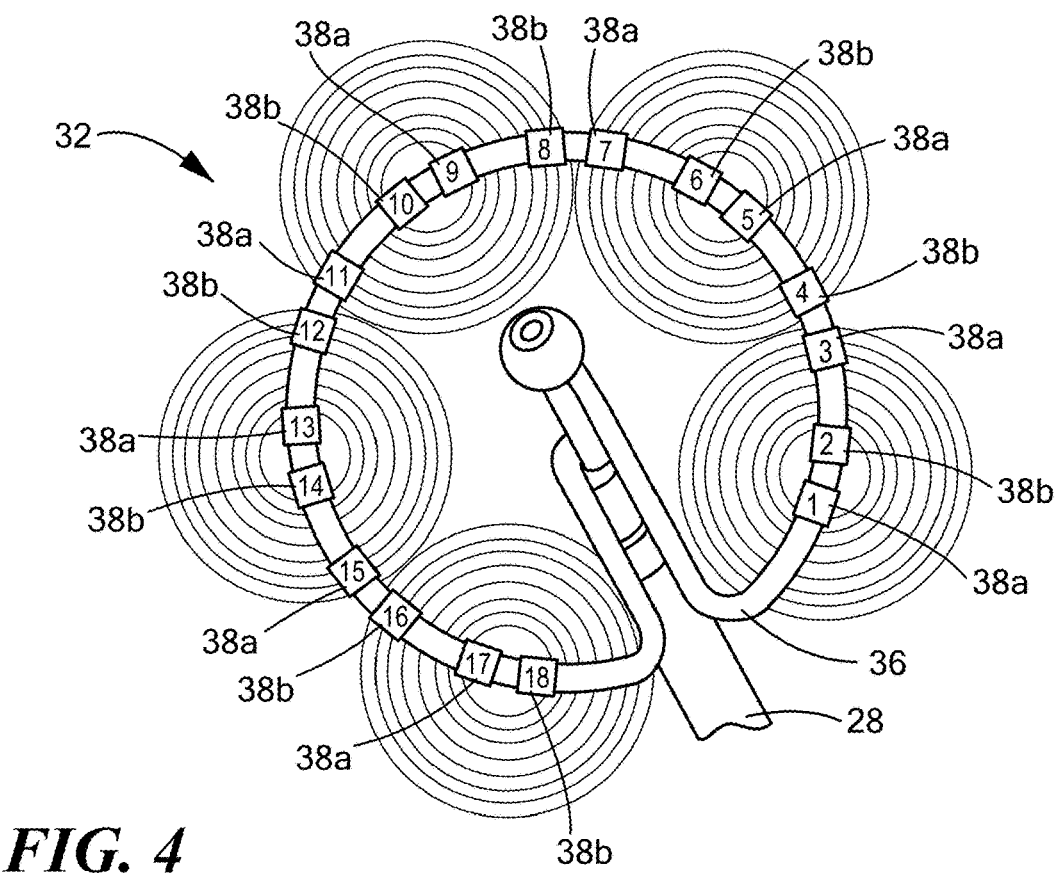
FIG. 4 shows a distal portion of the medical device having the first configuration of electrodes, the electrodes delivering ablation energy in a second delivery pattern.
Figure 5:
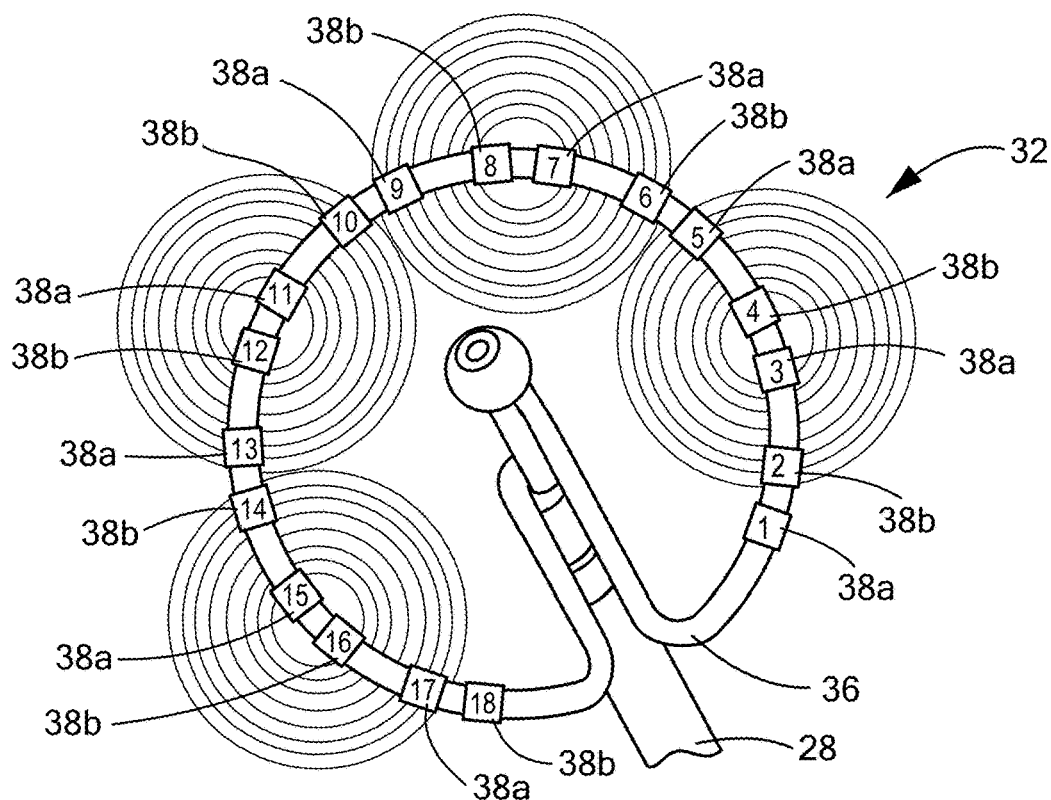
FIG. 5 shows a distal portion of the medical device having the first configuration of electrodes, the electrodes delivering ablation energy in a third delivery pattern.

As shown in FIGS. 4 and 5, a larger ablative effect may be achieved by delivering ablation energy through every other electrode pair 38a, 38b. For example, as shown in FIG. 4, ablation energy may be delivered through only the first electrode pair 38a, 38b (Electrodes 1 and 2), the third electrode pair 38a, 38b (Electrodes 5 and 6), the fifth electrode pair 38a, 38b (Electrodes 9 and 10), the seventh electrode pair 38a, 38b (Electrodes 13 and 14), and the ninth electrode pair 38a, 38b (Electrodes 17 and 18). Alternatively, as shown in FIG. 5, ablation energy may be delivered through only the second electrode pair 38a, 38b (Electrodes 3 and 4), the fourth electrode pair 38a, 38b (Electrodes 7 and 8), the sixth electrode pair 38a, 38b (Electrodes 11 and 12), and the eighth electrode pair 38a, 38b (Electrodes 15 and 16).

Figure 6:
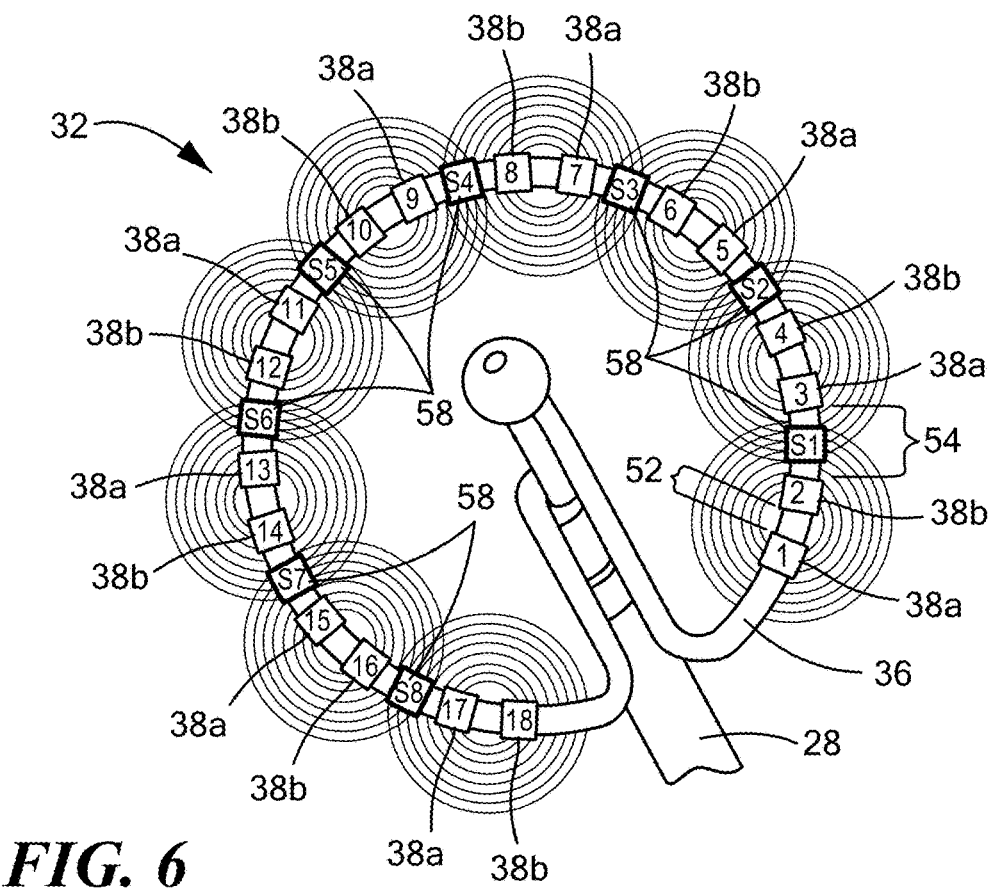
FIG. 6 shows a distal portion of the medical device having a second configuration of electrodes.

Referring now to FIG. 6, a treatment element 32 having a second configuration of electrodes 38 is shown. The treatment element 32 may include a carrier element 36 bearing a plurality of electrodes 38. As a non-limiting example, a first set of eighteen electrodes is shown in FIG. 6 (labeled with numbers 18, referred to herein as electrodes E1-E18), which have the same configuration and characteristics as those shown in FIGS. 3-5. However, the configuration shown in FIG. 6 also includes a second set of electrodes 58 (labeled as SE1-SE8). Each electrode 58 of the second set may be the same size as electrodes 38 in the first set, for example, between approximately 1.0 mm and approximately 2.0 mm in length with a diameter that is larger than the diameter of the carrier element 36, such that the electrodes 38 protrude from the carrier element 36. Further, each electrode 58 of the second set may be located in the space 54 between adjacent pairs of electrodes 38a, 38b.

As described above for the configuration of FIG. 5, the device electrode distribution system 16 may allow bipolar EGM recording from the closely spaced electrode pairs by connecting each electrode 38 to the recording system 40 independently when ablation energy is not being delivered. Pulsed electric field ablation energy may be delivered in a manner that treats each closely spaced electrode pair 38a, 38b as a single electrode (that is, the two electrodes 38a, 38b of each pair may be electrically connected to each other). Further, the second set of electrodes 58 may be used for mapping purposes and/or recording of delivered electric pulses, as such, may remain disconnected from the generator 14 and recording system 40 during pulsed electric field ablation energy deliveries.

Figure 7:
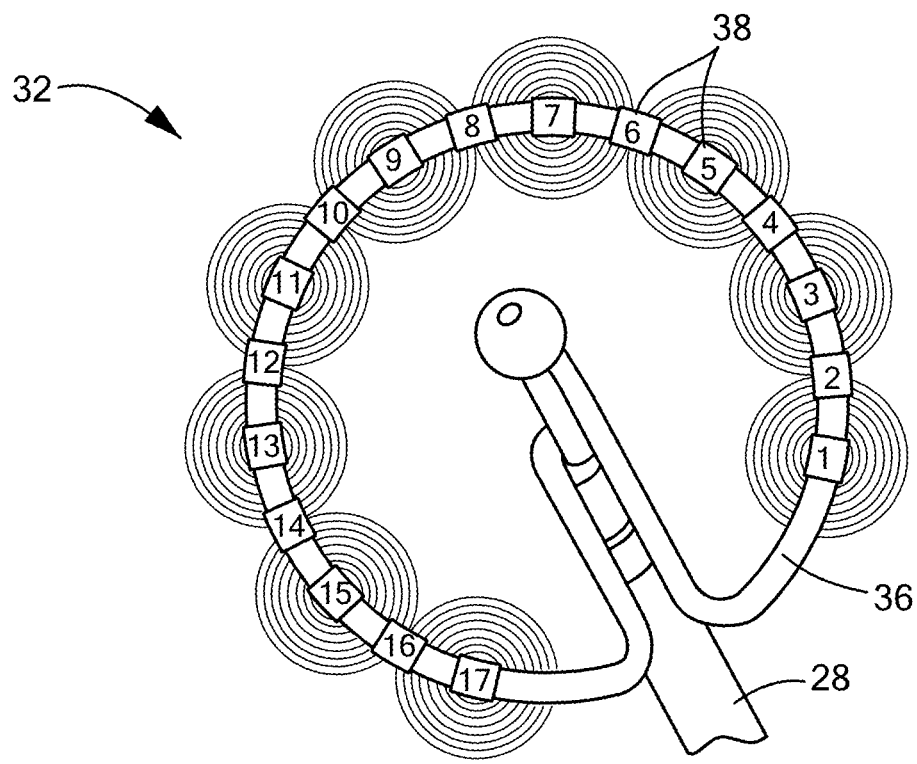
FIG. 7 shows a distal portion of the medical device having a third configuration of electrodes, the electrodes delivering ablation energy in a first delivery pattern of a first ablation mode.
Figure 8:
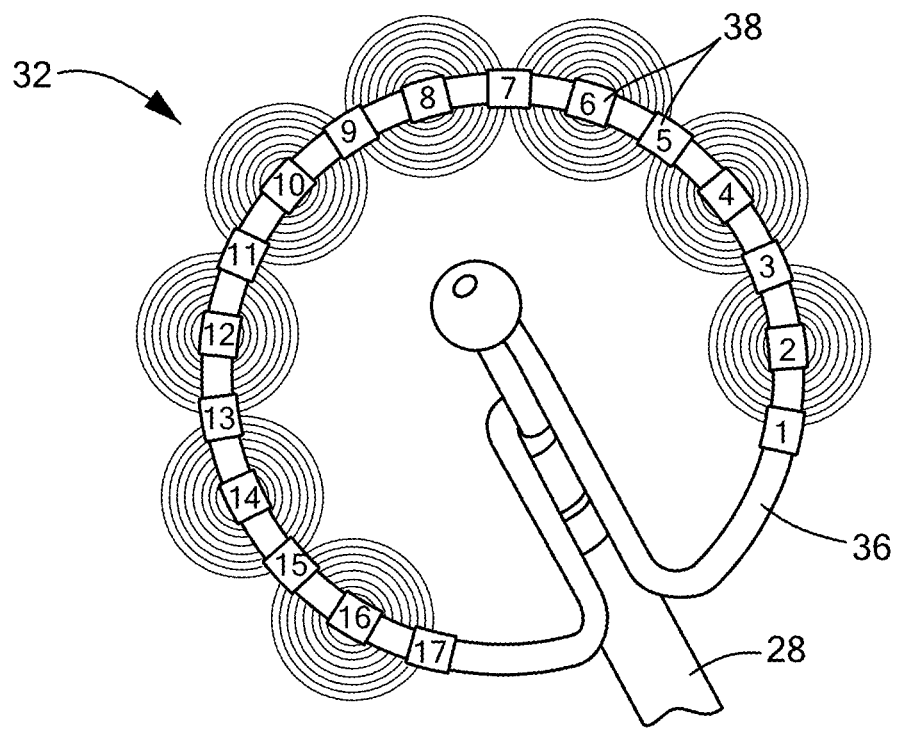
FIG. 8 shows the distal portion of the medical device having the third configuration of electrodes, the electrodes delivering ablation energy in a second delivery pattern of the first ablation mode.

Referring now to FIGS. 7 and 8, a treatment element 32 having a third configuration of electrodes 38 is shown, with a first energy delivery pattern of a first ablation mode being shown in FIG. 7 and a second energy delivery pattern of the first ablation mode being shown in FIG. 8. The treatment element 32 may include a carrier element 36 bearing a plurality of electrodes 38. As a non-limiting example, seventeen electrodes 38 may be used (labeled with numbers 1-17 in FIGS. 7 and 8, referred to herein as electrodes E1-E17). Each electrode 38 may be relatively small, between approximately 1.5 mm and approximately 2.5 mm in length, and may have a diameter that is larger than the diameter of the carrier element 36, such that the electrodes 38 protrude from the carrier element 36. The space 54 between adjacent electrodes 38 may also be relatively small, for example, between approximately 1.0 mm and approximately 2.0 mm. As a non-limiting example, a configuration including a carrier element 36 bearing seventeen electrodes 38, each electrode being approximately 2 mm wide and the space 54 between adjacent electrodes 38 being approximately 1.5 mm, may allow for high-resolution intracardiac electrogram recording while allowing high voltage pulsed electric field deliveries for ablation to be delivered through every other electrode. Energizing every other electrode 38 may allow for a greater separation distance of approximately 5 mm between active electrodes, thereby driving the electric field deeper into the underlying tissue and creating a deeper ablation lesion. In either delivery pattern discussed below, EGM recording would be allowed from all electrodes prior to ablation, between ablation energy deliveries, and/or after ablation to provide high-resolution EGM signals.

A first delivery pattern is shown in FIG. 7, in which ablation energy is delivered only to the odd electrodes (that is, electrodes E1, E3, E5, E7, E9, E11, E13, E15, and E17). Further, electrodes E1, E5, E9, E13, and E17 are connected to a first polarity of the generator 14 (for example, the negative polarity) while electrodes E3, E7, E11, and E15 are connected to a second polarity of the generator 14 (for example, the positive polarity). After a train of biphasic pulses has been delivered using only the odd electrodes, the device electrode distribution system 16 may then switch to using only the even numbered electrodes (that is, electrodes E2, E4, E6, E8, E10, E12, E14, and E16) for a similar train of pulses. This second delivery pattern is shown in FIG. 8. Specifically, electrodes E2, E6, E10, and E14 are connected to the negative polarity of the generator 14 while electrodes E4, E8, E12, and E16 are connected to the positive polarity of the generator 14. The two pulse train deliveries (that is, delivery by odd electrodes only then delivery by even electrodes only) may be automated by the generator 14 and device electrode distribution system 16, such that the two patterns would be delivered in rapid succession. Further, although delivery using the odd electrodes before the even electrodes has been described, it will be understood that the even electrodes may be used before the odd electrodes in an alternative method of delivery. It will also be understood that the polarity delivered through particular groups of electrodes may be the opposite of what is described above (e.g., the first polarity being the positive polarity and the second polarity being the negative polarity), as long as the polarity of every other active electrode is the same and polarities of adjacent active electrodes are different. It will also be understood that when referring to positive or negative electrode polarities, this may mean that such electrodes with opposite designations are energized at opposite polarities during each of the alternating positive or negative applied voltages in biphasic alternative pulsed energy deliveries.

The treatment element may make contact with myocardial or other target tissue at a portion of the circumference of each of the electrodes 38, while the remaining portion of the circumference of each of the electrodes 38 is in contact only with blood. To maximize the quality of EGM recordings during mapping and to minimize the delivery of excess electrical current to the blood during energy deliveries, the non-tissue-facing surfaces of each electrode 38 (that is, the portion of the circumference that is in contact with blood) may be electrically nonconductive. For example, the non-tissue-facing surface of each electrode 38 may be composed of electrically non-conductive material and/or may be coated with an electrical insulator or oxide to minimize or prevent electric signals or current from passing into or out of that surface of the electrode 38. This directional conductivity may provide the treatment element 32 with improved rejection of far-field intracardiac electrogram signals while reducing the electrical current and total delivered energy when ablative energy is delivered.

Figure 9:
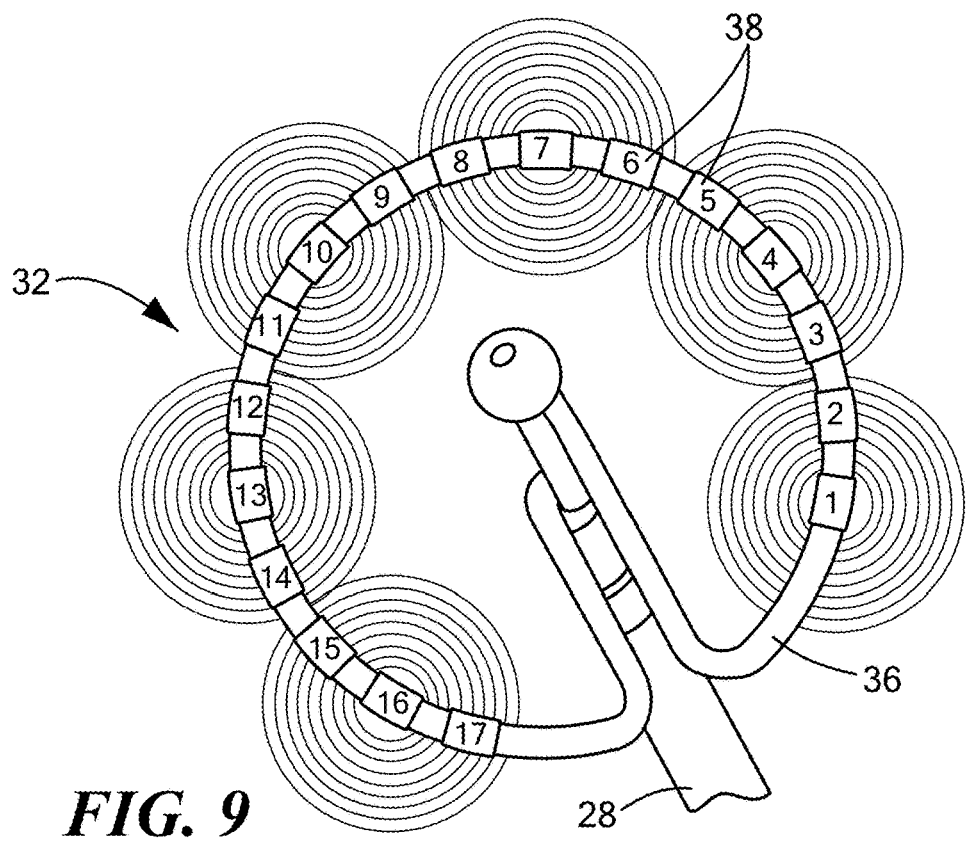
FIG. 9 shows the distal portion of the medical device having the third configuration of electrodes, the electrodes delivering ablation energy in a first delivery pattern of a second ablation mode.
Figure 10:
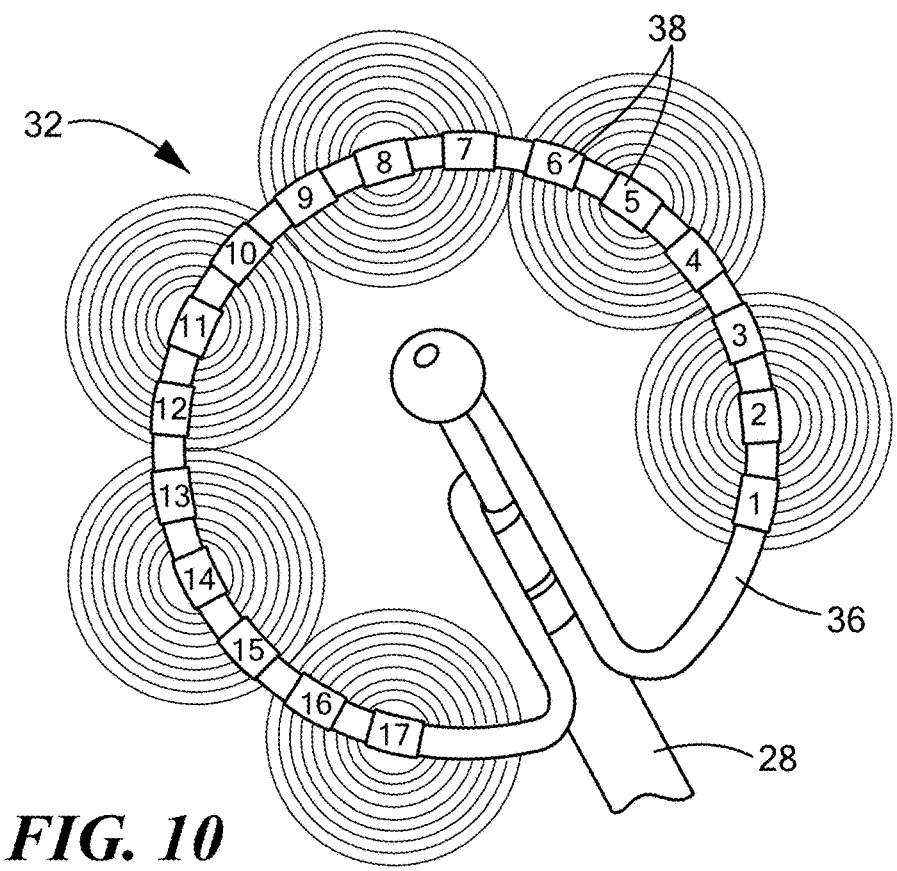
FIG. 10 shows the distal portion of the medical device having the third configuration of electrodes, the electrodes delivering ablation energy in a second delivery pattern of the second ablation mode.
Figure 11:
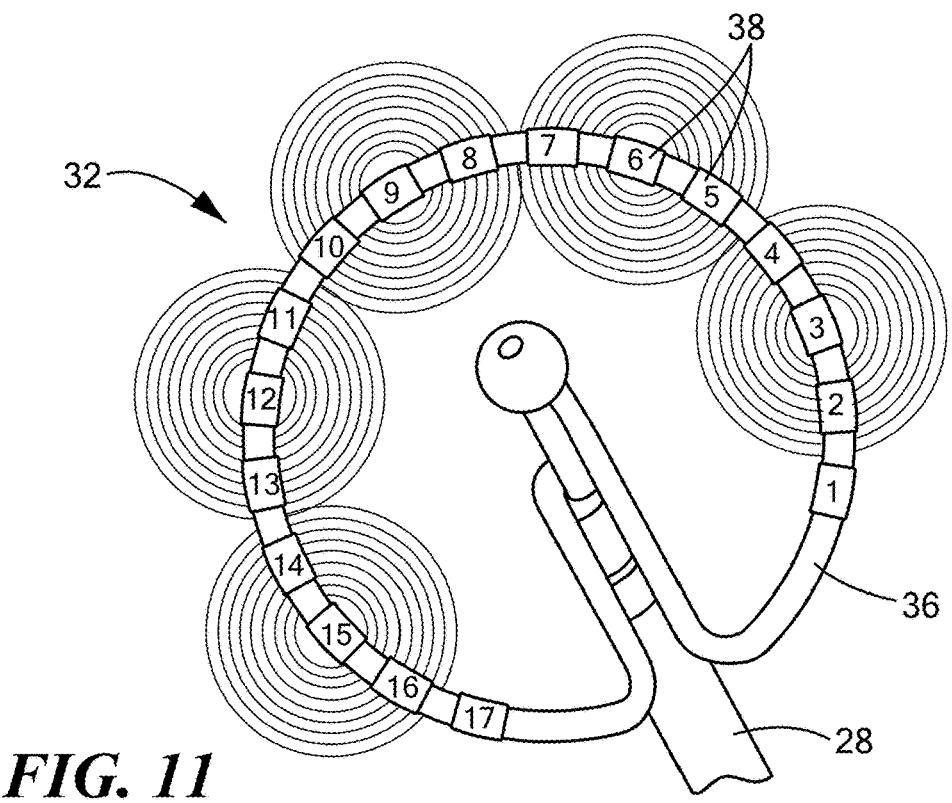
FIG. 11 shows the distal portion of the medical device having the third configuration of electrodes, the electrodes delivering ablation energy in a third delivery pattern of the second ablation mode.

Referring now to FIGS. 9-11, a treatment element 32 having the third configuration of electrodes 38 is shown, with a first energy delivery pattern of a second ablation mode being shown in FIG. 9, a second energy delivery pattern of the second ablation mode being shown in FIG. 10, and a third energy delivery pattern of the second ablation mode being shown in FIG. 11. The treatment element 32 may include a carrier element 36 bearing a plurality of electrodes 38. As a non-limiting example, seventeen electrodes 38 may be used (labeled with numbers 1-17 in FIGS. 9-11, referred to herein as electrodes E1-E17), which have the same configuration and characteristics as those shown in FIGS. 7 and 8.

The first delivery pattern is shown in FIG. 9, in which ablation energy is delivered through a set of active electrodes that includes only every third electrode (that is, E1, E4, E7, E10, E13, and E16). Further, electrodes E1, E7, and E13 are connected to a first polarity of the generator 14 (for example, the negative polarity) while electrodes E4, E10, and E16 are connected to a second polarity of the generator 14 (for example, the positive polarity).

After a train of biphasic pulses has been delivered in the first delivery pattern, the device electrode distribution system 16 may then switch to delivery in the second delivery pattern (shown in FIG. 10). In the second delivery pattern, the set of active electrodes is shifted by one electrode such that electrodes E2, E5, E8, E11, E14, and E17 are activated. Similar to the first delivery pattern shown in FIG. 9, electrodes E2, E8, and E14 are connected to a first polarity (for example, the positive polarity) of the generator 14 and electrodes E5, E11, and E17 are connected to a second polarity (for example, the negative polarity). After a train of biphasic pulses has been delivered in the second delivery pattern, the device electrode distribution system 16 may then switch to delivery in the third delivery pattern (shown in FIG. 11). In the third delivery pattern, the set of active electrodes is again shifted by one electrode such that electrodes E3, E6, E9, E12, and E15 are activated. Similar to the first delivery pattern shown in FIG. 9, electrodes E3, E9, and E15 are connected to a first polarity (for example, the positive polarity) of the generator 14 and electrodes E6 and E12 are connected to a second polarity (for example, the negative polarity). The use of multiple delivery patterns at the same positioning of the treatment element 32 on the tissue surface may cause the underlying tissue to experience multiple electric field vector directions, thereby causing a larger percentage of cells exposed to electroporation and effectively electroporated. This automated delivery may be accomplished by switching which electrodes are connected to each polarity from the generator 14 with high-voltage vacuum relays or the like.

Figure 12:
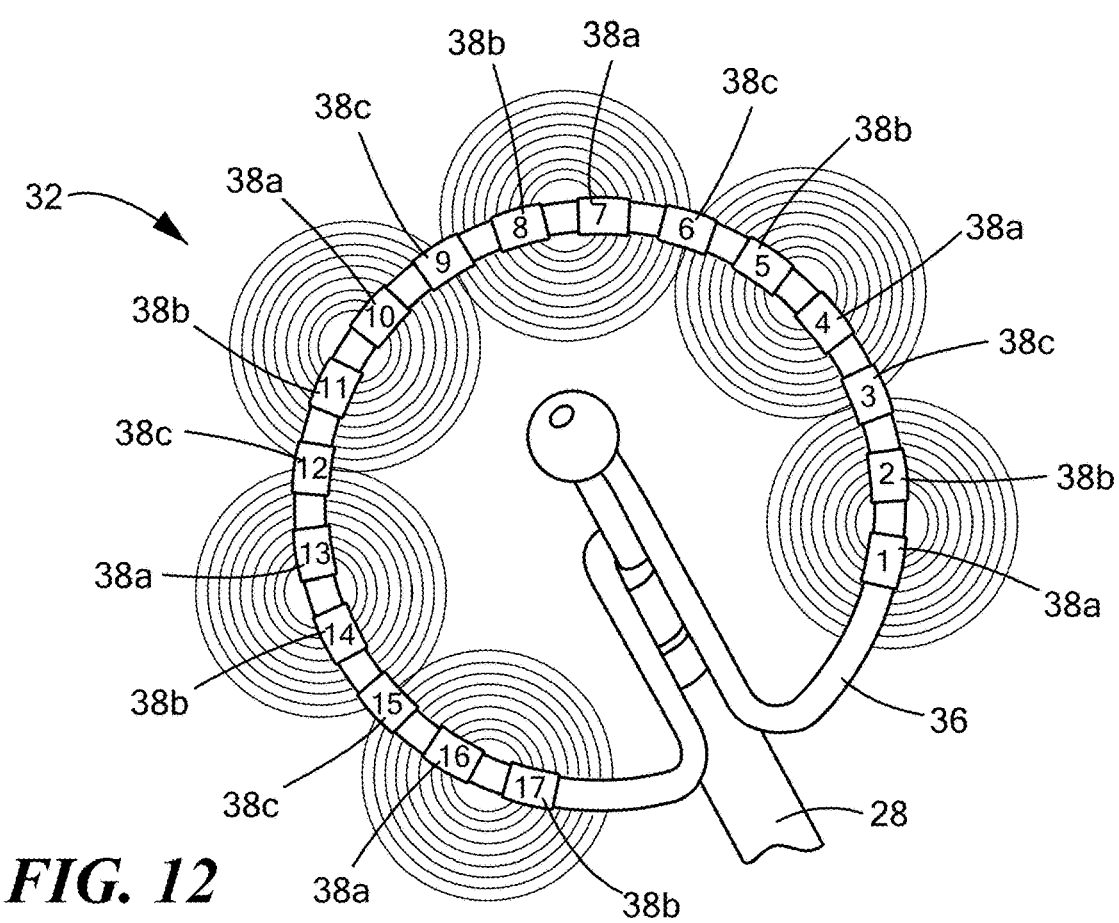
FIG. 12 shows the distal portion of the medical device having the third configuration of electrodes, the electrodes delivering ablation energy in a first delivery pattern of a third ablation mode.
Figure 13:
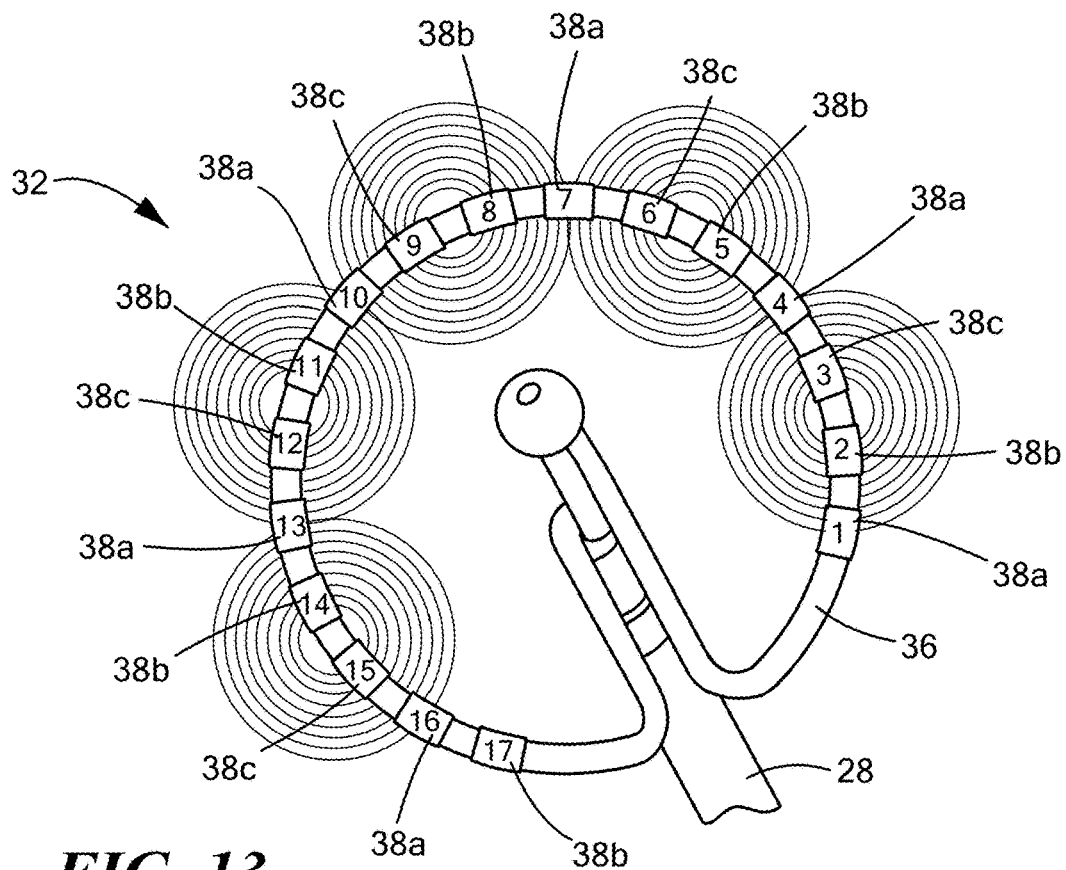
FIG. 13 shows the distal portion of the medical device having the third configuration of electrodes, the electrodes delivering ablation energy in a second delivery pattern of the third ablation mode.

Referring now to FIGS. 12 and 13, a treatment element 32 having the third configuration of electrodes 38 is shown, with a first energy delivery pattern of a third ablation mode being shown in FIG. 12 and a second energy delivery pattern of the third ablation mode being shown in FIG. 13. The treatment element 32 may include a carrier element 36 bearing a plurality of electrodes 38. As a non-limiting example, seventeen electrodes 38 may be used (labeled with numbers 1-17 in FIGS. 9-11, referred to herein as electrodes E1-E17), which have the same configuration and characteristics as those shown in FIGS. 7 and 8.

The first delivery pattern is shown in FIG. 12, in which ablation energy is delivered through a set of active electrodes that includes only two of every three electrodes 38. In particular, the first 38a and second 38b electrode of each electrode triplet may be treated as a single electrode and connected to a first polarity, whereas the third electrode 38c of each triplet is disconnected from the generator 14 (floating potential). Further, adjacent active pairs 38a, 38b may be connected to opposite polarities. For example, electrodes E1-E3 may form a first electrode triplet, in which electrodes E1 and E2 are both connected to a first polarity (for example, the negative polarity) and electrode E3 is disconnected. In this configuration, electrodes E1 and E2 perform as a single electrode. Electrodes E4-E6 may form a second electrode triplet, in which electrodes E4 and E5 are both connected to a second polarity (for example, the positive polarity) and electrode E6 is disconnected. In this configuration, electrodes E4 and E5 perform as a single electrode and operate to deliver bipolar energy (that is, energy delivered in bipolar mode) with the active electrode pair 38a, 38b of the adjacent electrode triplet, such as electrodes E1 and E2 of the first electrode triplet. Likewise, electrodes E7-E9 may form a third electrode triplet, in which electrodes E7 and E8 are both connected to the first polarity (for example, the negative polarity) and electrode E9 is disconnected. Electrodes E10-E12 may form a fourth electrode triplet, in which electrodes E10 and E11 are both connected to the second polarity (for example, the positive polarity) and electrode E12 is disconnected. Electrodes E13-E15 may form a fifth electrode triplet, in which electrodes E13 and E14 are both connected to the first polarity (for example, the negative polarity) and electrode E15 is disconnected. Finally, electrodes E16 and E17 may form an electrode pair, in which electrodes E16 and E17 are both connected to the second polarity (for example, the positive polarity). In this manner, the electrode pair E16 and E17 may operate to delivery bipolar energy with the active electrode pair 38a, 38b of the first electrode triplet (that is, electrodes E1 and E2).

After a train of biphasic pulses has been delivered in the first delivery pattern, the device electrode distribution system 16 may then switch to delivery in the second delivery pattern (shown in FIG. 13). In the second delivery pattern, the set of active electrodes is shifted counterclockwise by one electrode. Although energy may still be delivered through the first 38a and second 38b electrode of each electrode triplet, which electrodes 38a, 38b may be treated as a single electrode and connected to a first polarity, and the first electrode 38a of each triplet may still be disconnected from the generator 14 (floating potential), the pattern distribution over electrodes E1-E17 advances by one electrode. For example, electrodes E2-E4 may form a first electrode triplet, in which electrodes E2 and E3 are both connected to a first polarity (for example, the negative polarity) and electrode E4 is disconnected. Electrodes E5-E7 may form a second electrode triplet, in which electrodes E5 and E6 are both connected to a second polarity (for example, the positive polarity) and electrode E7 is disconnected. In this configuration, electrodes E5 and E6 perform as a single electrode and operate to deliver bipolar energy with the active electrode pair 38a, 38b of the adjacent electrode triplet, such as electrodes E2 and E3 of the first electrode triplet. Likewise, electrodes E8-E10 may form a third electrode triplet, in which electrodes E8 and E9 are both connected to the first polarity (for example, the negative polarity) and electrode E1° is disconnected. Electrodes E11-E13 may form a fourth electrode triplet, in which electrodes E11 and E12 are both connected to the second polarity (for example, the positive polarity) and electrode E13 is disconnected. Electrodes E14-E16 may form a fifth electrode triplet, in which electrodes E14 and E15 are both connected to the first polarity (for example, the negative polarity) and electrode E16 is disconnected. Finally, electrodes E16, E17, and E1 may each be disconnected.

Although not shown, the device electrode distribution system 16 may then switch to delivery in a third delivery pattern, in which the set of active electrodes is further shifted counterclockwise by one electrode. For example, electrodes E3-E5 may form a first electrode triplet, in which electrodes E3 and E4 are both connected to a first polarity (for example, the negative polarity) and electrode E5 is disconnected. Electrodes E6-E8 may form a second electrode triplet, in which electrodes E6 and E7 are both connected to a second polarity (for example, the positive polarity) and electrode E8 is disconnected. Electrodes E9-E11 may form a third electrode triplet, in which electrodes E9 and E10 are both connected to the first polarity (for example, the negative polarity) and electrode E11 is disconnected. Electrodes E12-E14 may form a fourth electrode triplet, in which electrodes E12 and E13 are both connected to the second polarity (for example, the positive polarity) and electrode E14 is disconnected. Electrodes E15-E17 may form a fifth electrode triplet, in which electrodes E15 and E16 are both connected to the first polarity (for example, the negative polarity) and electrode E17 is disconnected. Finally, electrodes E1 and E2 may each be disconnected. Such shifting between the first and second delivery patterns, and optionally the third delivery pattern, may provide more electric field vector directions, thereby causing a larger percentage of cells exposed to electroporation and effectively electroporated.

Figure 14:
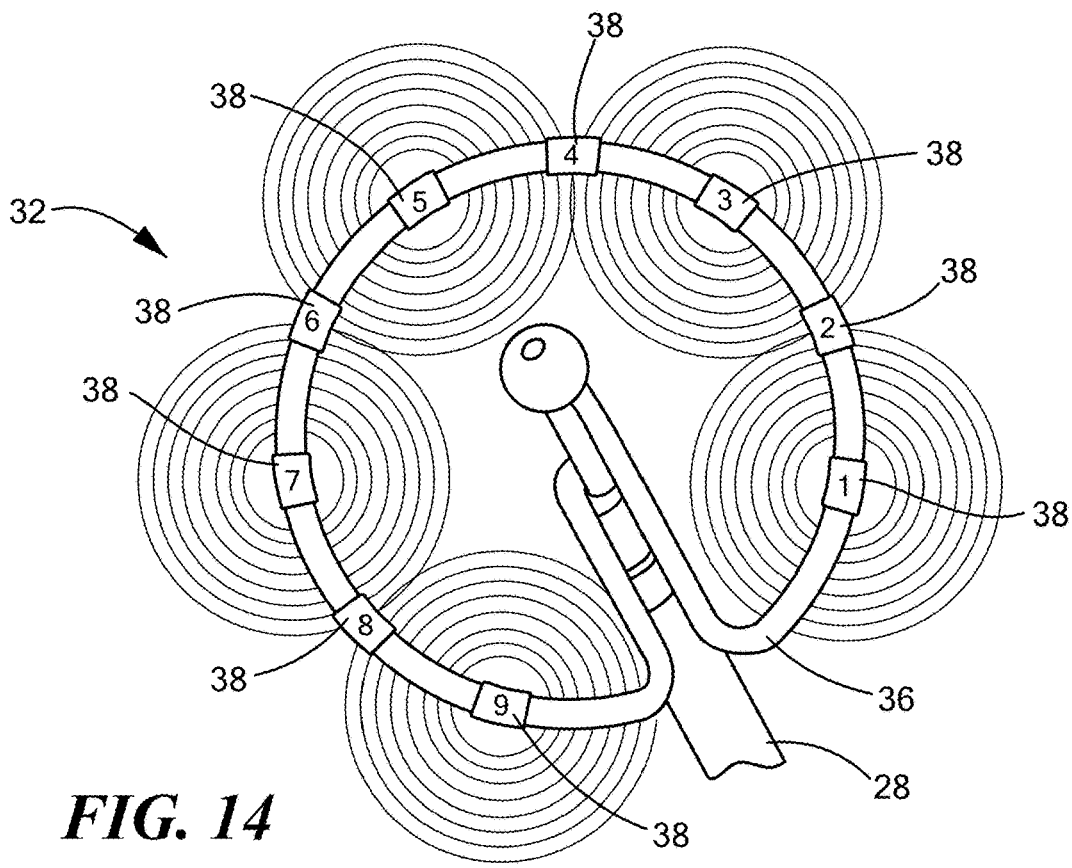
FIG. 14 shows the distal portion of the medical device having a fourth configuration of electrodes, the electrodes delivering ablation energy in a first delivery pattern.
Figure 15:
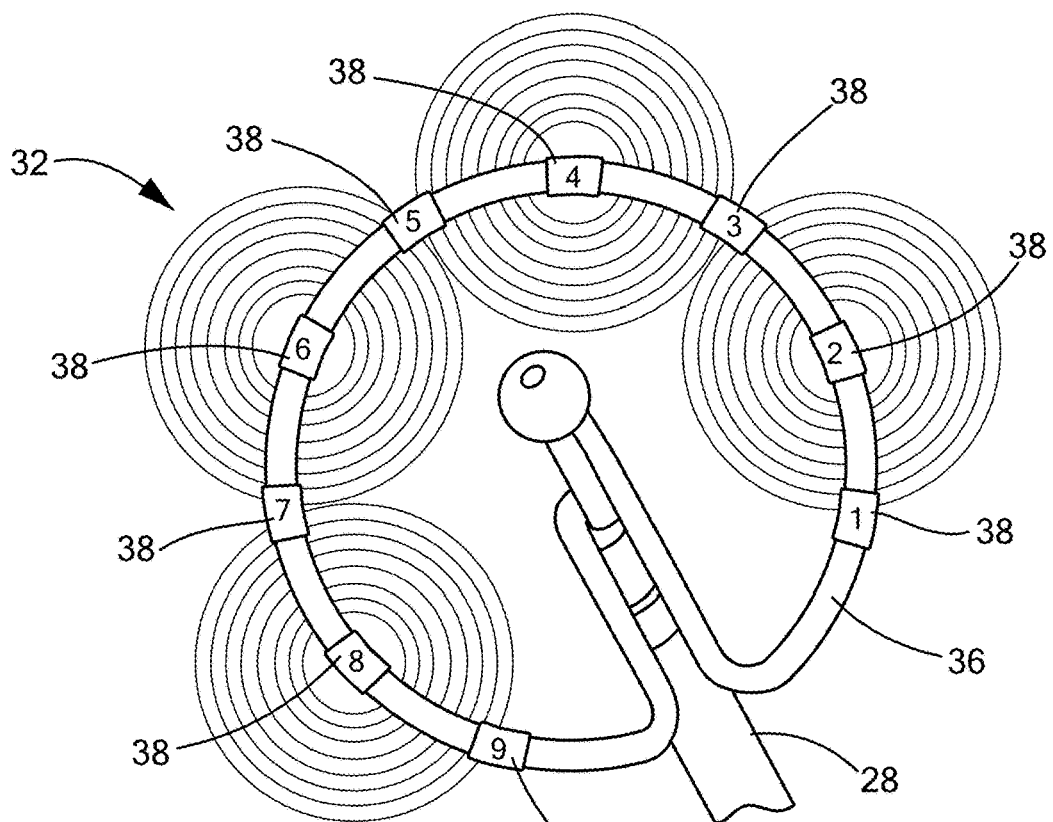
FIG. 15 shows the distal portion of the medical device having the fourth configuration of electrodes, the electrodes delivering ablation energy in a second delivery pattern.

Referring now to FIGS. 14 and 15, a treatment element 32 having a fourth configuration of electrodes 38 is shown, with a first energy delivery pattern being shown in FIG. 14 and a second energy delivery pattern being shown in FIG. 15. The treatment element 32 may include a carrier element 36 bearing a plurality of electrodes 38. As a non-limiting example, nine electrodes 38 may be used (labeled with numbers 1-9 in FIGS. 14 and 15, referred to herein as electrodes E1-E9). Each electrode 38 may be relatively small, between approximately 1.5 mm and approximately 2.5 mm in length, and may have a diameter that is larger than the diameter of the carrier element 36, such that the electrodes 38 protrude from the carrier element 36. Conversely, the space 54 between adjacent electrodes 38 may be relatively large, for example, approximately 3 mm or larger. Because of this spacing configuration, all electrodes E1-E9 may be activated with alternating polarities to deliver energy in a bipolar mode, which delivery pattern is not shown in the figures. Alternatively, as shown in FIGS. 14 and 15, energy may be delivered through only odd electrodes 38 or to only even electrodes 38. The wider electrode spacing shown in FIGS. 14 and 15 may provide the engineering advantage of having fewer electrode wires within the carrier element 36.

In the first delivery pattern shown in FIG. 14, ablation energy is delivered only to the odd electrodes (that is, electrodes E1, E3, E5, E7, and E9. Further, electrodes E1, E5, and E9 are connected to a first polarity of the generator 14 (for example, the negative polarity) while electrodes E3 and E7 are connected to a second polarity of the generator 14 (for example, the positive polarity). After a train of biphasic pulses has been delivered using only the odd electrodes, the device electrode distribution system 16 may then switch to using only the even numbered electrodes (that is, electrodes E2, E4, E6, and E8) for a similar train of pulses. This second delivery pattern is shown in FIG. 15. Specifically, electrodes E2 and E6 are connected to the negative polarity of the generator 14 while electrodes E4 and E8 are connected to the positive polarity of the generator 14. The two pulse train deliveries (that is, delivery by odd electrodes only then delivery by even electrodes only) may be automated by the generator 14 and device electrode distribution system 16, such that the two patterns would be delivered in rapid succession. Further, although delivery using the odd electrodes before the even electrodes has been described, it will be understood that the even electrodes may be used before the odd electrodes in an alternative method of delivery. It will also be understood that the polarity delivered through particular groups of electrodes may be the opposite of what is described above (e.g., the first polarity being the positive polarity and the second polarity being the negative polarity), as long as the polarity of every other active electrode is the same and polarities of adjacent active electrodes are different.

Figure 16:
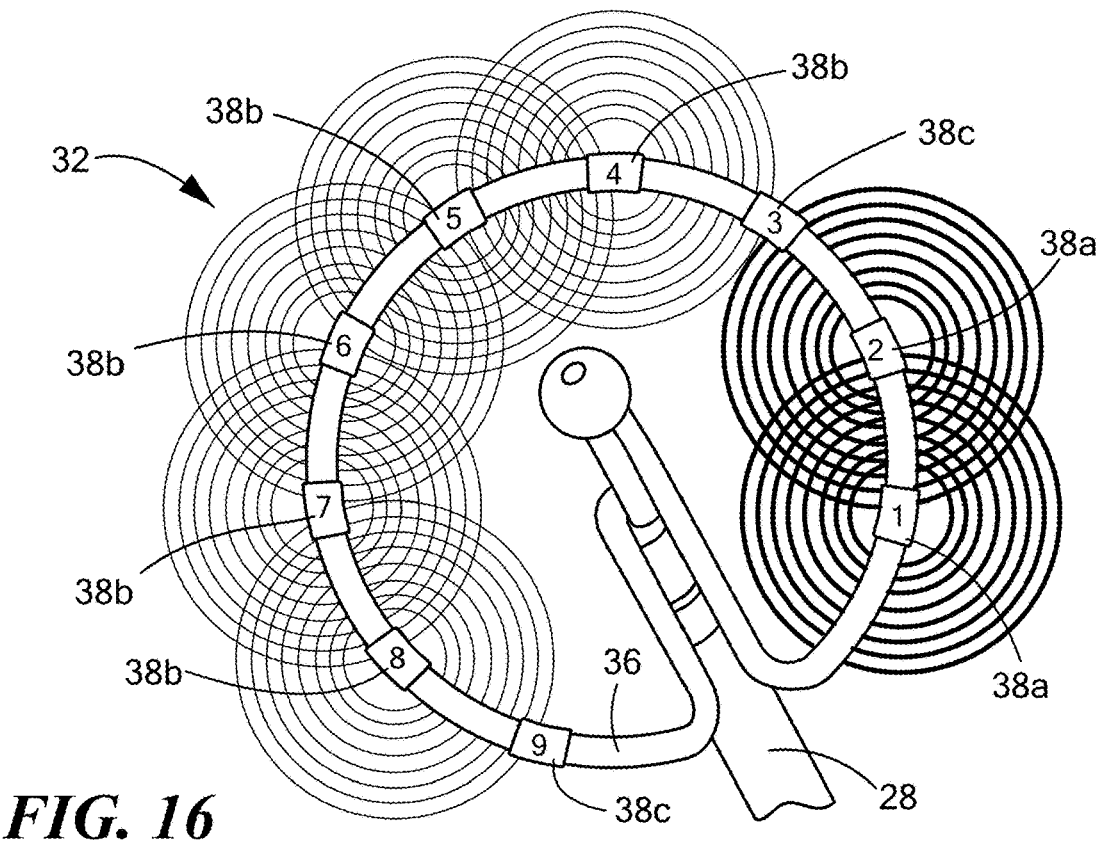
FIG. 16 shows the distal portion of the medical device having the fourth configuration of electrodes, the electrodes delivering ablation energy in a third delivery pattern.
Figure 17:
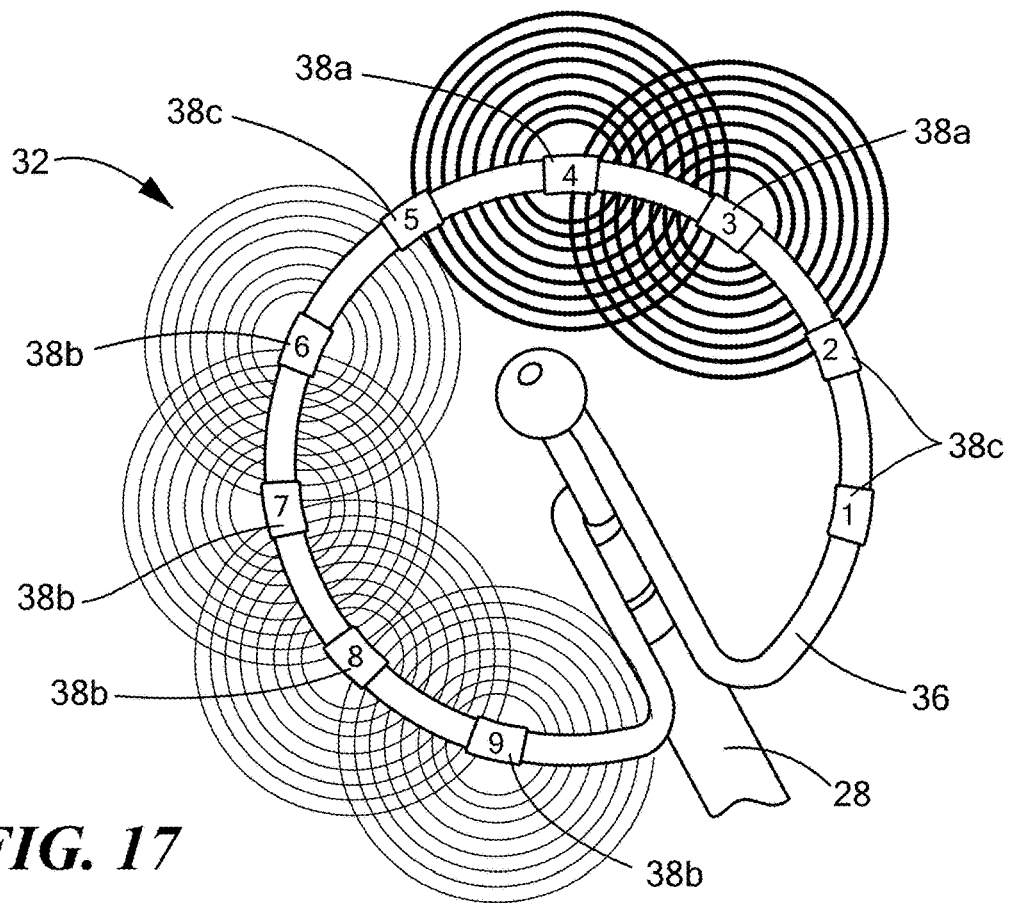
FIG. 17 shows the distal portion of the medical device having the fourth configuration of electrodes, the electrodes delivering ablation energy in a fourth delivery pattern.
Figure 18:
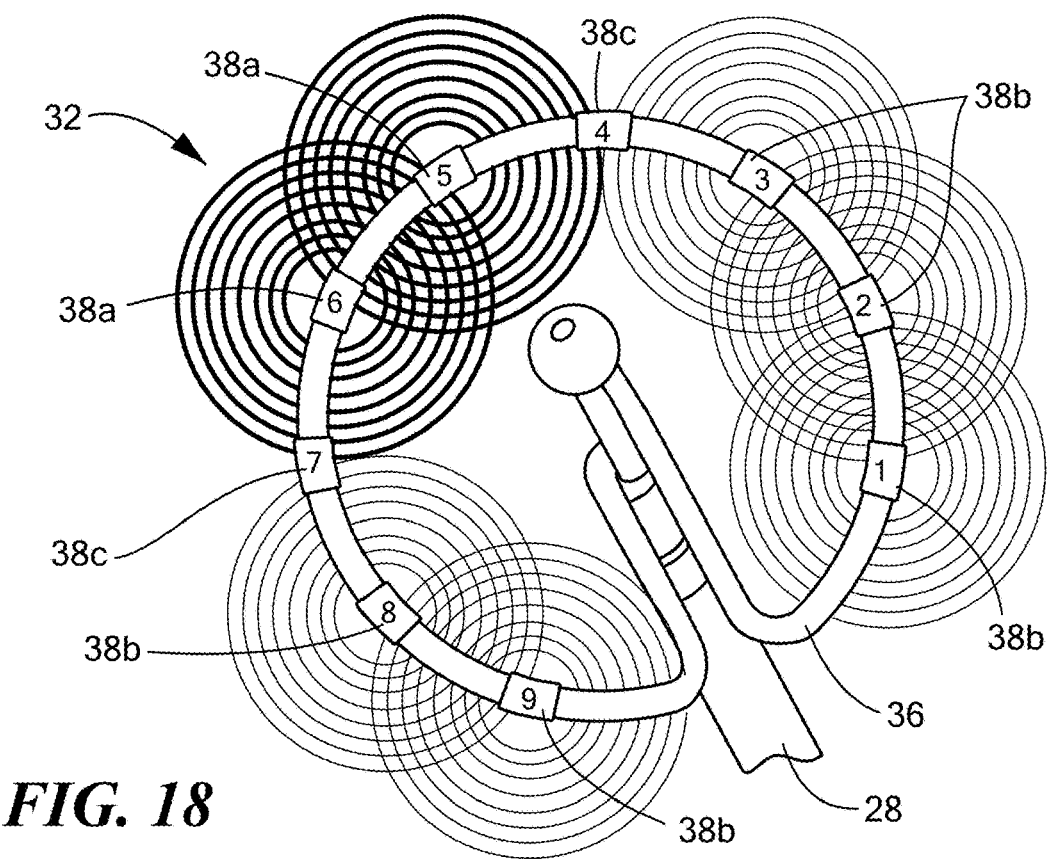
FIG. 18 shows the distal portion of the medical device having the fourth configuration of electrodes, the electrodes delivering ablation energy in a fifth delivery pattern.
Figure 19:
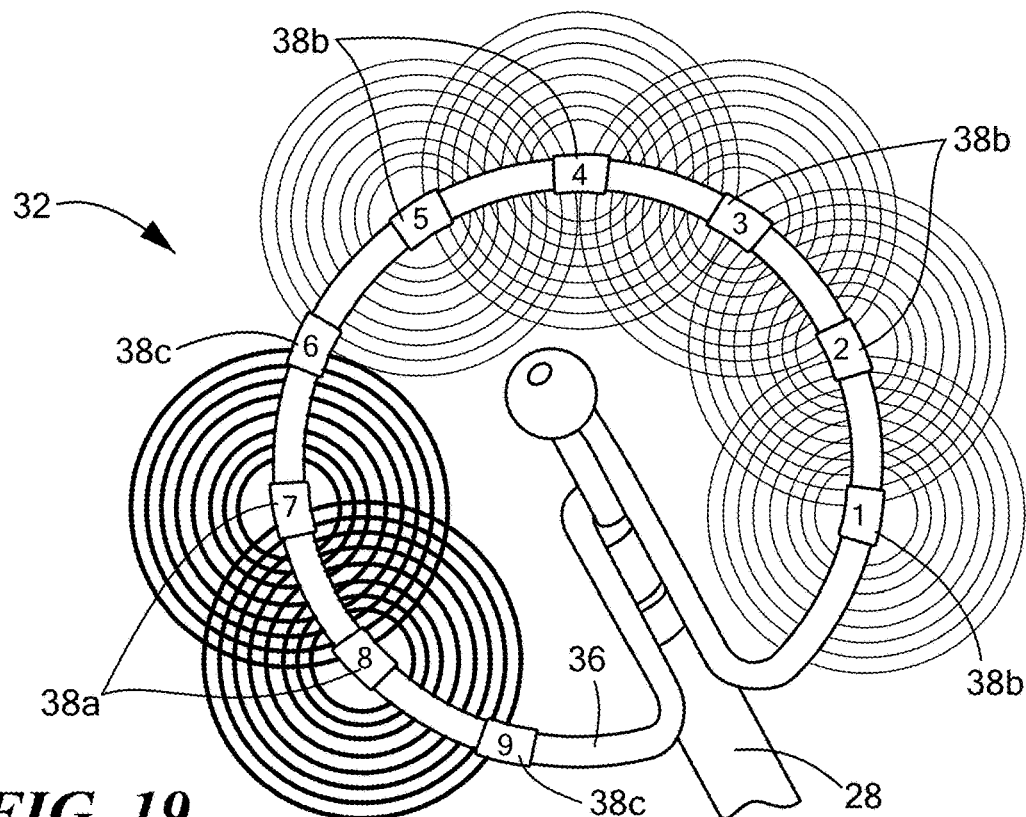
FIG. 19 shows the distal portion of the medical device having the fourth configuration of electrodes, the electrodes delivering ablation energy in a sixth delivery pattern.
Figure 20:
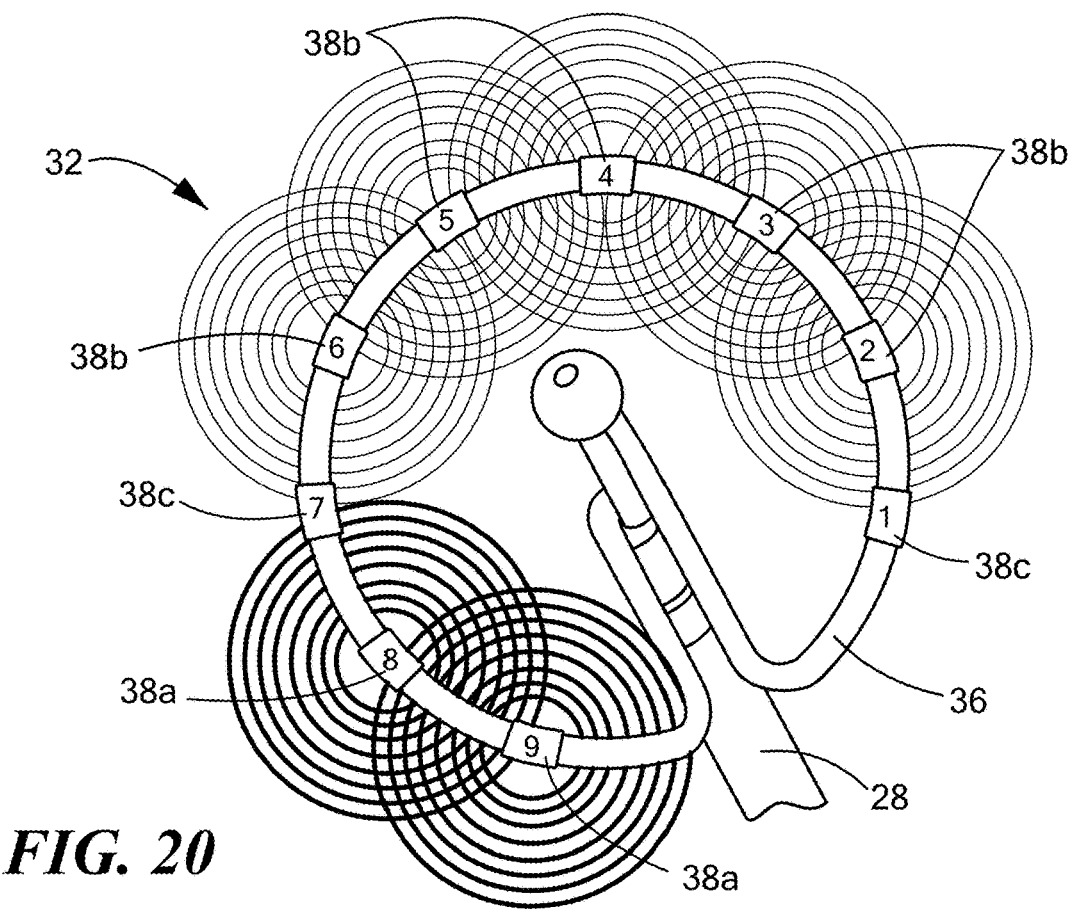
FIG. 20 shows the distal portion of the medical device having the fourth configuration of electrodes, the electrodes delivering ablation energy in an seventh delivery pattern.
Figure 21:
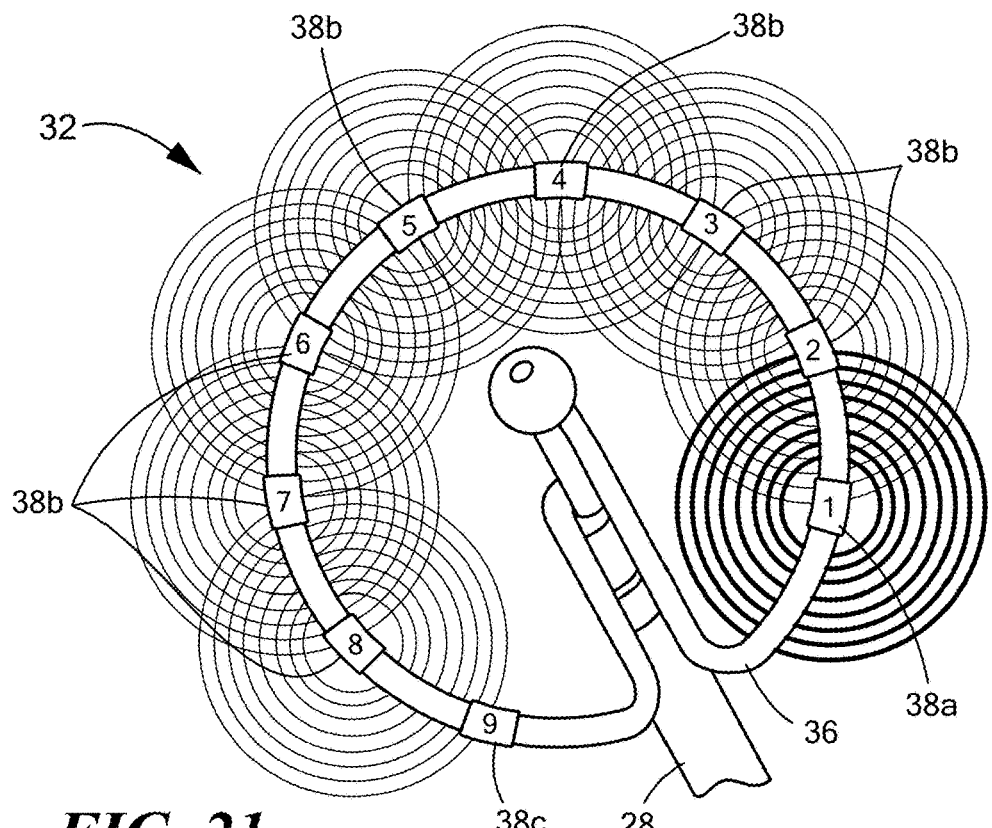
FIG. 21 shows the distal portion of the medical device having the fourth configuration of electrodes, the electrodes delivering ablation energy in a eighth delivery pattern.
Figure 22:
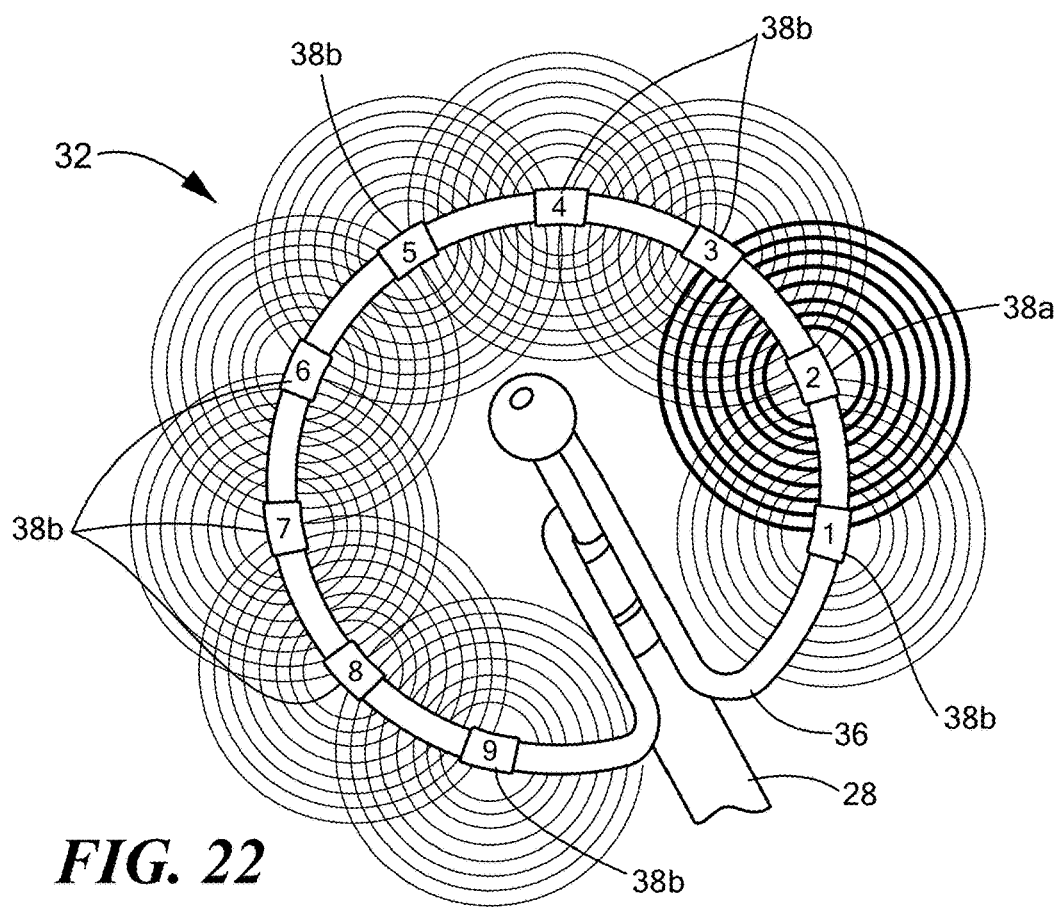
FIG. 22 shows the distal portion of the medical device having the fourth configuration of electrodes, the electrodes delivering ablation energy in a ninth delivery pattern.
Figure 23:
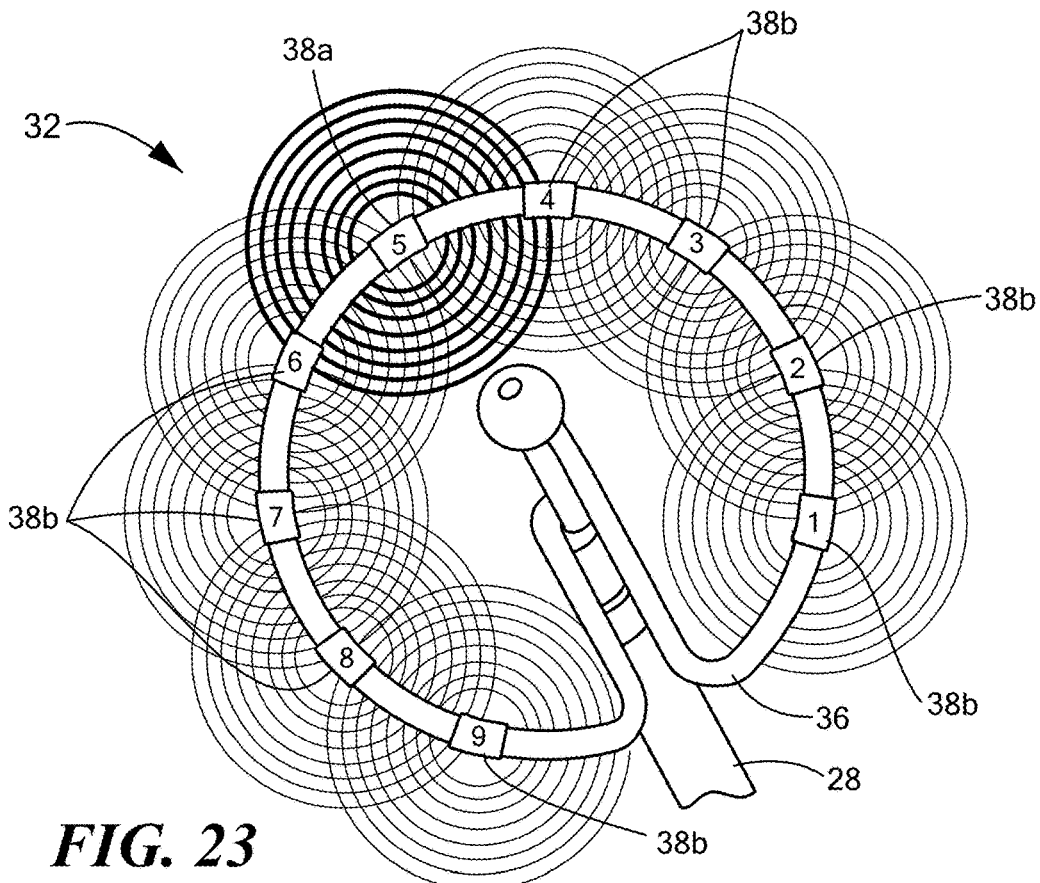
FIG. 23 shows the distal portion of the medical device having the fourth configuration of electrodes, the electrodes delivering ablation energy in a tenth delivery pattern.
Figure 24:
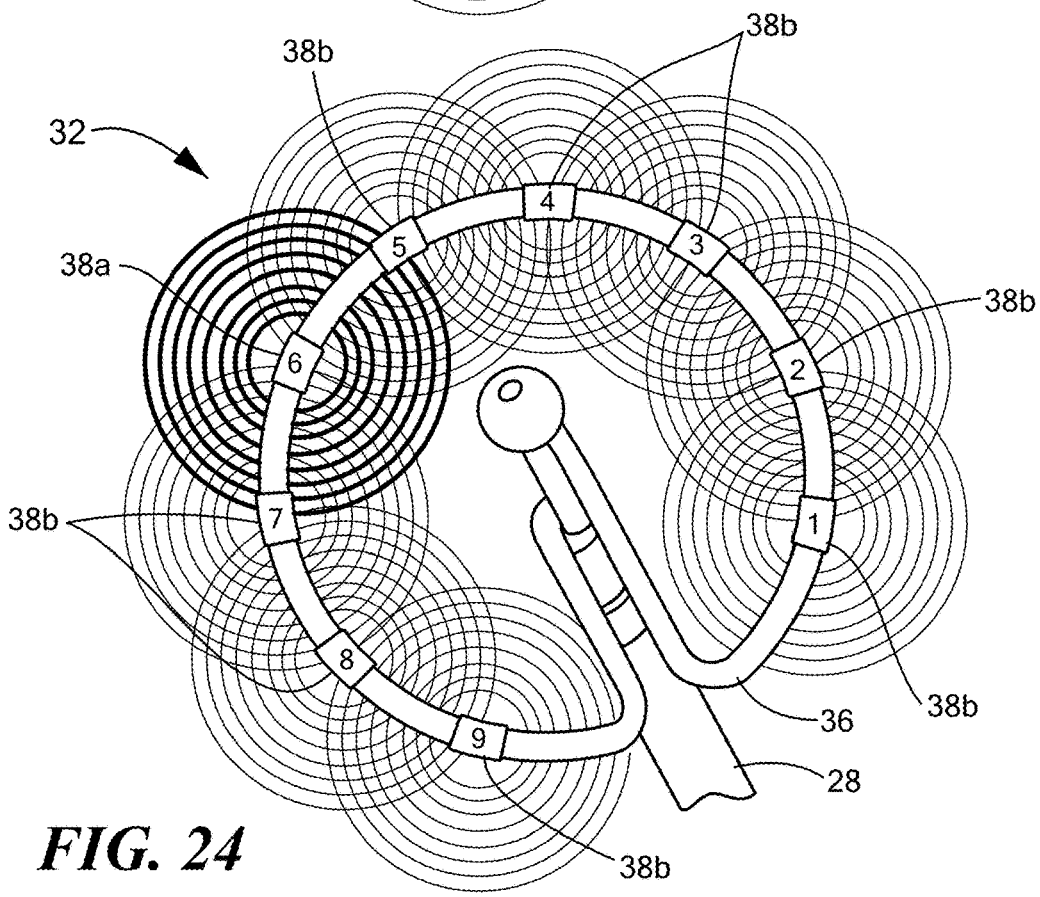
FIG. 24 shows the distal portion of the medical device having the fourth configuration of electrodes, the electrodes delivering ablation energy in an eleventh delivery pattern.
Figure 25:
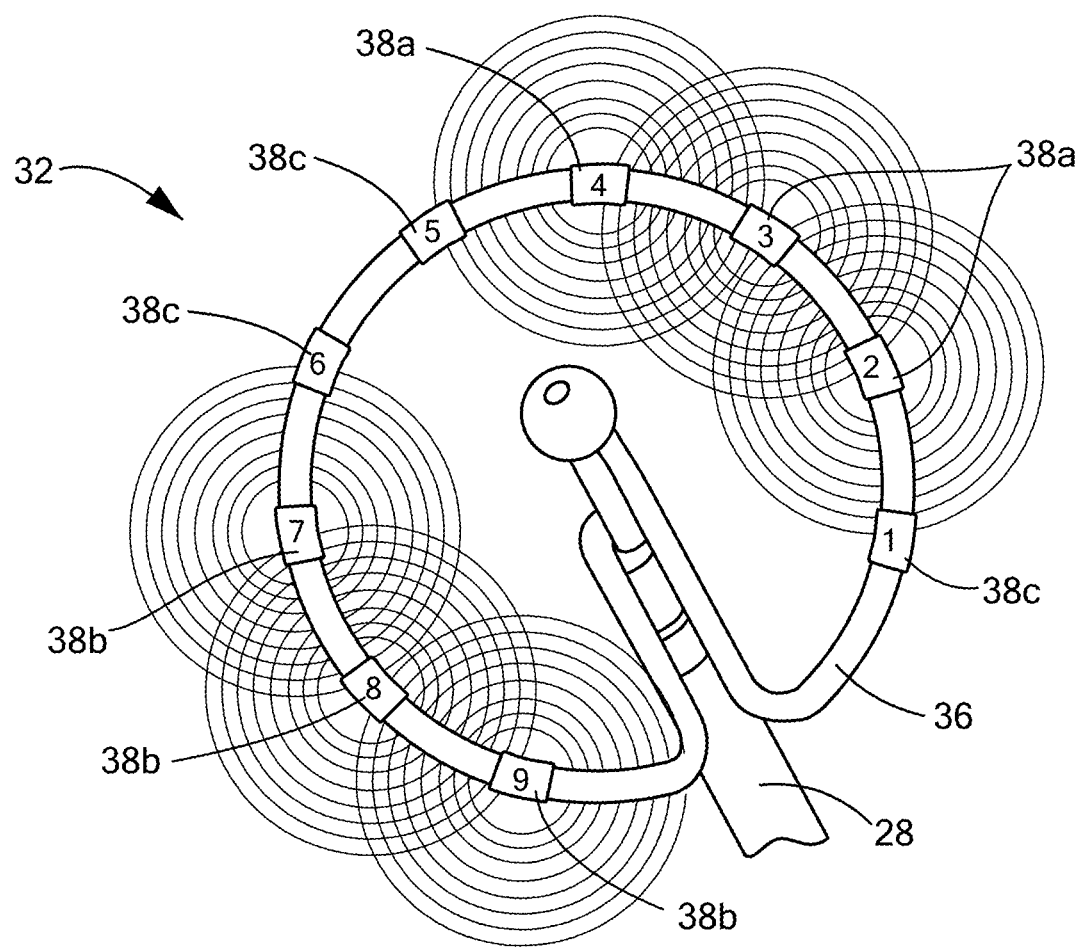
FIG. 25 shows the distal portion of the medical device having the fourth configuration of electrodes, the electrodes delivering ablation energy in a twelfth delivery pattern.

Referring now to FIGS. 16-25, a treatment element 32 having the fourth configuration of electrodes 38 is shown (as shown and described in FIGS. 14 and 15), with a third energy delivery pattern being shown in FIG. 16, a fourth energy delivery pattern being shown in FIG. 17, a fifth energy delivery pattern being shown in FIG. 18, a sixth energy delivery pattern being shown in FIG. 19, a seventh energy delivery pattern being shown in FIG. 20, an eighth energy delivery pattern being shown in FIG. 21, a ninth delivery pattern being shown in FIG. 22, a tenth delivery pattern being shown in FIG. 23, an eleventh delivery pattern being shown in FIG. 24, and a twelfth delivery pattern being shown in FIG. 25. As shown in FIGS. 16-25, the ablation energy may be delivered through the electrodes 38 in a gradient distribution in which one or more electrodes produce a greater ablative effect than the other electrodes.

Figure 26:
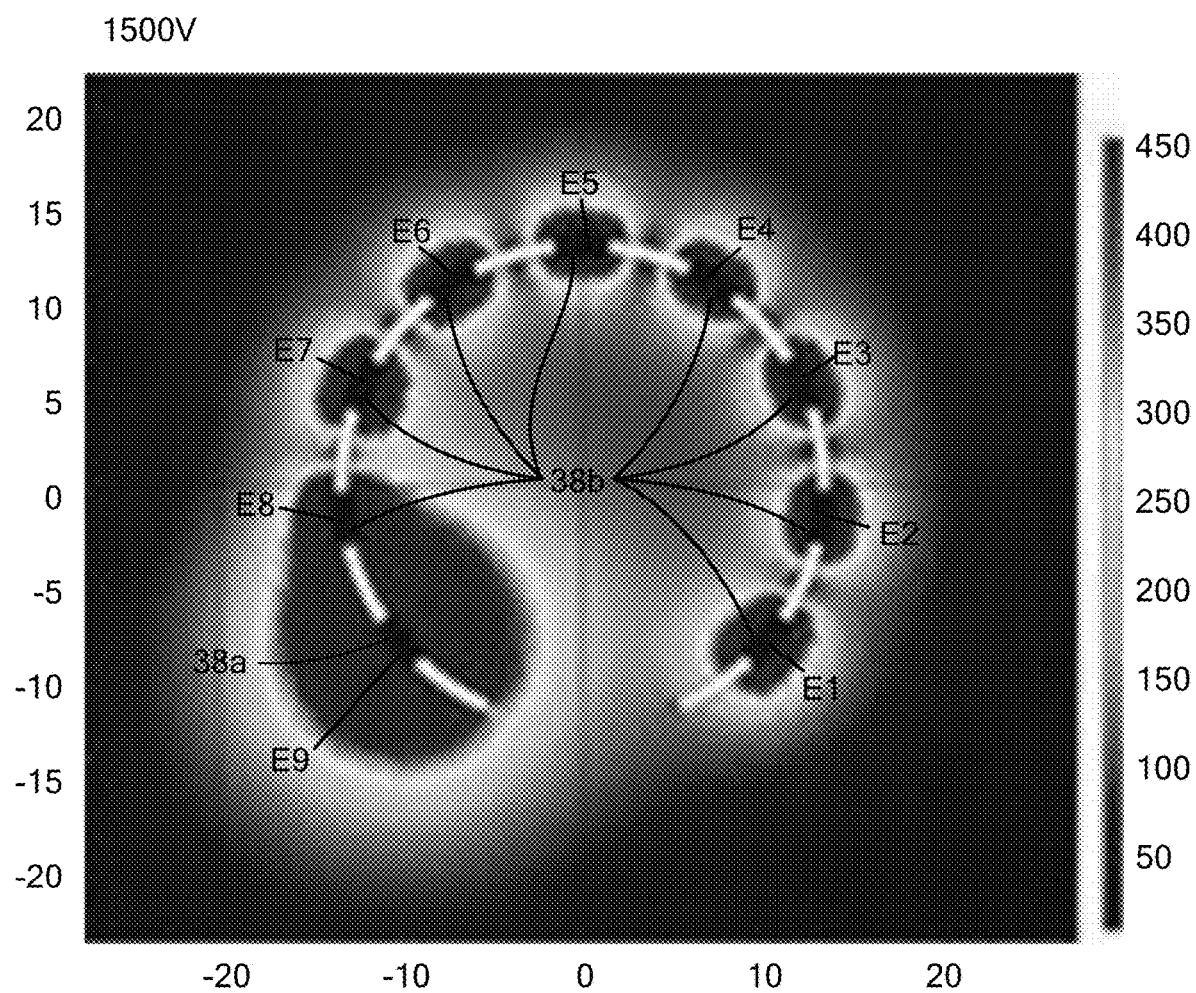
FIG. 26 shows an exemplary ablation pattern created by delivering energy in a gradient distribution.

In the delivery patterns shown in FIGS. 16-25, energy is delivered in bipolar mode. For illustration, the electrodes producing the energy fields (that is, the concentric circles surrounding the electrodes) shown with bold lines represent electrodes connected to a first polarity of the energy generator 14, such as a positive polarity, and the electrodes producing the energy fields shown with lighter lines represent electrodes connected to an opposite, second polarity of the energy generator 14, such as a negative polarity. Current flows back and forth between the electrodes connected to the first polarity and the electrodes connected to the second polarity. For example, the treatment element 32 may include a first plurality of electrodes 38 that is connected to a first polarity of the generator 14 and a second plurality of electrodes 38 that is connected to a second polarity of the generator 14, with the first plurality and second plurality of electrodes including a different number of electrodes. If fewer electrodes 38 are connected to one polarity as the number of electrodes 38 connected to the opposite polarity (that is, if the first plurality of electrodes includes fewer electrodes than the second plurality of electrodes), the electrodes 38 connected to the one polarity may transmit a relatively greater amount of energy than the electrodes 38 connected to the opposite polarity and, therefore, produce deeper lesions in the adjacent tissue (for example, as shown in FIG. 26). Further, the device electrode distribution system 16 may record and/or monitor the instantaneous and/or total amount of energy delivered by each of the electrodes 38 and alert the user if, for example, an excessive amount of energy is transmitted through any of the electrodes 38.

In the third delivery pattern shown in FIG. 16, ablation energy is delivered through fewer than all electrodes 38. As a non-limiting example, a first plurality of electrodes 38a (electrodes E1 and E2) are connected to a first polarity of the generator 14, such as a positive polarity, and a second plurality of electrodes 38b (electrodes E4-E8) are connected to an opposite, second polarity of the generator 14, such as a negative polarity, and the first plurality of electrodes 38a and the second plurality of electrodes 38b include different number of electrodes. In the non-limiting example shown in FIG. 16, the first plurality of electrodes 38a includes fewer electrodes than the second plurality 38b of electrodes. A third plurality of electrodes 38c (electrodes E3 and E9) may be electrically disconnected from the generator 14. The disconnection of the electrodes 38c may be desirable when applying high voltages of, for example, in the range of 1200-1500 V or greater between electrodes 38a and 38b. Depending on the electrode spacing and geometry, other ranges of pulses may be used that are considerably lower or higher than this range. As a non-limiting example, voltages of between 300-900 V, or between 1600-2500 V, may be used. Also, for example, if the distance between electrodes is smaller, lower amplitudes may be used. If energy is applied at lower voltages below this range, it may be desirable to connect electrodes 38c to the same polarity as electrodes 38b. Each of the electrodes 38b in the second plurality passes current to each of the electrodes 38a in the first plurality, which means, in this example, that two electrodes (E1 and E2) receive energy from five electrodes (E4-E8). Conversely, each of the electrodes 38a in the first plurality passes current to each of the electrodes 38b in the second plurality, which means that five electrodes (E4-E8) receive energy from only two electrodes (E1 and E2). Accordingly, electrodes E1 and E2 in the first plurality of electrodes 38a may be expected to overheat more easily than electrodes E4-E8 in the second plurality of electrodes 38b, depending on the voltage being delivered. Therefore, electrodes E3 and E9 may be electrically disconnected to the generator 14 to reduce current density adjacent to and protect against overheating electrodes E1 and E2. Additionally or alternatively, the device may include a cooling element, such as a Peltier cooler, to reduce the temperature of the electrodes and/or treated tissue. In the exemplary energy delivery pattern shown in FIG. 26, only one electrode 38a (E9) is connected to a first polarity, whereas eight electrodes 38b (E1-E8) are connected to a second polarity. As a result, electrode E9 may produce an increased ablation area in adjacent tissue. Although FIG. 26 shows only a single electrode being connected to a first plurality and does not show adjacent electrodes being electrically disconnected from the generator 14, it will be understood that FIG. 26 is for illustration only and does not limit the delivery configurations shown and described herein. Additionally, if the voltage being delivered by the electrodes 38 is below a threshold level, the electrodes 38 may be unlikely to overheat and it therefore may be unnecessary to electrically disconnect one or more electrodes 38 from the generator 14.

FIGS. 17-25 show further examples of energy delivery patterns in a first plurality of electrodes 38a connected to a first polarity includes fewer electrodes than a second plurality of electrodes 38b connected to a second polarity, which allows energy delivered through the electrodes 38a of the first plurality to extend more deeply into adjacent tissue. In the non-limiting embodiments of energy delivery patterns shown in FIGS. 17-20, the first plurality of electrodes 38a includes two adjacent electrodes, the second plurality of electrodes 38b includes five adjacent electrodes, and the third plurality of electrodes 38c includes two electrodes, with a each of the two electrodes 38c being between the first plurality 38a and the second plurality 38b. In other words, the first plurality of electrodes 38a includes fewer electrodes than the second plurality of electrodes 38b, and one electrode 38c between the first and second pluralities of electrodes 38a, 38b on either side of the first plurality of electrodes 38a is electrically disconnected from the generator 14. The electrically disconnected electrodes 38c may prevent the first plurality of electrodes 38a from overheating, if necessary, as described above.

In the eighth, ninth, tenth, and eleventh delivery patterns shown in FIGS. 21-24, ablation energy may be delivered through all electrodes 38 or fewer than all electrodes 38. In either case, a single first 38a electrode is connected to a first polarity of the generator 14, such as a positive polarity, and a plurality of electrodes 38b are connected to an opposite, second polarity of the generator 14, such as a negative polarity. A second single electrode 38c may be electrically disconnected from the generator 14 (for example, electrode E9 is electrically disconnected from the generator 14 in FIG. 21). Each of the electrodes 38b in the plurality of electrodes passes current to the single electrically connected electrode 38a, which means, in this example, that one electrode receives energy from seven or eight electrodes. Conversely, the single electrode 38a passes current to each of the electrodes 38b in the plurality of electrodes, which means that seven or eight electrodes receive energy from only one electrode. Accordingly, the single 38a may produce an increased ablation area in adjacent tissue.

In the non-limiting embodiment shown in FIG. 21, electrode E1 is the single electrode 38a that is electrically connected to the first polarity of the generator 14, whereas electrodes E2-E8 are the plurality of electrodes 38b that are electrically connected to the second polarity of the generator 14. In the non-limiting embodiment shown in FIG. 22, electrode E2 is the single electrode 38a that is electrically connected to the first polarity of the generator 14, whereas electrodes E1 and E3-E9 are the plurality of electrodes 38b that are electrically connected to the second polarity of the generator 14. These two delivery patterns shown in FIGS. 21 and 22 may be delivered sequentially such that focused energy is delivered first through electrode E1 and then through electrode E2, and this sequence may be repeated any number of times and/or combined with other delivery patterns. For example, the generator 14 may be programmed and configured to deliver ablation energy according to a predefined cycle, in which a first train of pulses (for example, 100 pulses) is delivered with focus on delivery through electrode E1 followed immediately (for example, within 20 ms) by a second train of pulses (for example, 100 pulses) delivered with focus on delivery through electrode E2. This cycle may be repeated or focused energy may be delivered through other electrodes.

In the non-limiting embodiment shown in FIG. 23, electrode E5 is the single electrode 38a that is electrically connected to the first polarity of the generator 14, whereas electrodes E1-E4 and E6-E9 are the plurality of electrodes 38b that are electrically connected to the second polarity of the generator 14. In the non-limiting embodiment shown in FIG. 24, electrode E6 is the single electrode 38a that is electrically connected to the first polarity of the generator 14, whereas electrodes E1-E5 and E7-E9 are the plurality of electrodes 38b that are electrically connected to the second polarity of the generator 14. These two delivery patterns shown in FIGS. 23 and 24 may be delivered sequentially such that focused energy is delivered first through electrode E5 and then through electrode E6, and this sequence may be repeated any number of times and/or combined with other delivery patterns. For example, the generator 14 may be programmed and configured to deliver ablation energy according to a predefined cycle, in which a first train of pulses (for example, 100 pulses) is delivered with focus on delivery through electrode E5 followed immediately (within 20 ms) by a second train of pulses (for example, 100 pulses) delivered with focus on delivery through electrode E6. This cycle may be repeated or focused energy may be delivered through other electrodes.

It will be understood that any of the first, second, and third pluralities of electrodes 38a, 38b, 38c may include more or fewer electrodes than those shown in FIGS. 16-25. For example, FIG. 21 shows a further energy delivery configuration in which the treatment element 32 may include a first plurality of electrodes 38a that is connected to a first polarity of the generator 14, such as a positive polarity (for example, electrodes E2-E4 as shown in FIG. 25) and a second polarity of electrodes 38b is connected to a second polarity of the generator 14, such as a negative polarity (for example, electrodes E7-E9 as shown in FIG. 25). The treatment element 32 may also include a third plurality of electrodes 38c that is electrically disconnected from the generator 14, with at least one electrode 38c being between the first and second pluralities of electrodes 38a, 38b. As a non-limiting example, FIG. 25 shows a group of two adjacent electrodes 38c (electrodes E5 and E6) of the third plurality of electrodes being between the first and second pluralities of electrodes 38a, 38b (that is between a first end of the first plurality 38a, electrode E4, and a second end of the second plurality 38b, electrode E7), and a single electrode 38c (electrode E1) being between the first and second pluralities of electrodes 38a, 38b (that is, between the second end of the first plurality, electrode E2, and the first end of the second plurality 38b, electrode E9). A single electrode 38c (electrode E1) between electrodes E1 and E9 may be electrically disconnected from the generator 14 and yet produce the same effect against electrode overheating because the treatment element 32, at least in the exemplary configuration shown in FIGS. 17-25, may include a wider gap between electrodes E1 and E9 than between any of the other electrodes, due to the structure of the treatment element 32.

Further, the carrier element 36 of the treatment element 32 may have an expanded shape that is at least substantially circular. The first plurality of electrodes 38a may be at a first location on the carrier element 36 and the second plurality of electrodes 38b may be at a second location on the carrier element 36 that is approximately 180° from the first location, with the third plurality of electrodes 38c being divide between two locations that are between the first plurality of electrodes 38a and the second plurality of electrodes 38b. In other words, an imaginary center point of the first plurality of electrodes 38a may be at least substantially opposite an imaginary center point of the second plurality of electrodes 38b. In the energy delivery configuration shown in FIG. 25, current may flow from one side of the treatment element 32 to the opposite side of the treatment element 32, thereby creating an ablation pattern that is at least substantially linear. In other words, the lesion may be at least substantially linear, or rectangular, as opposed to annular or at least substantially annular, as shown in FIG. 26.

Specific electrodes may selectively be connected or disconnected from one of the first and second polarities of the generator 14 in order to achieve a desired ablation pattern. For example, one or more of the energy delivery patterns shown in FIGS. 16-25 may be used in a procedure to produce a desired ablation pattern. Additionally or alternatively, the energy delivery patterns shown in FIGS. 16-20 may be used sequentially to produce an ablation pattern that is at least substantially circular. Switching between energy delivery patterns may be accomplished by the device electrode distribution system 16 discussed above. Additionally or alternatively, biphasic energy may be delivered through the electrodes 38, whereby each electrode 38 may sequentially be connected to a first polarity of the generator 14 and then a second polarity of the generator 14. In other words, an electrode 38 is not limited to being connected only to one of the first and second polarity of the generator 14. It may be desirable to sequentially deliver pulse trains using more than one of the various electrode polarity combinations shown in FIGS. 16-25. By sequentially delivering fields using different vector patterns, the electroporation effect may be enhanced to affect a greater percentage of the cells in the target tissue area. The sequential use of multiple field vector patterns may be automated through the processor 46 that controls energy delivery.

Referring now to FIGS. 27-39, electrode configurations are shown that may concentrate a delivered electric field for deeper and more precise lesion formation, while also allowing for the recordation of EGM signals. Like the treatment element 32 shown in FIGS. 1-25, the treatment element 32 of FIGS. 27, 28, and 30-39, when used with the system 10 described herein, provides the ability to control the delivery of ablation energy, including the depth and placement of lesions in tissue. The device shown in FIGS. 27, 28, and 30-39 may be used with the system shown in FIG. 1 and described above to deliver pulsed electric field electroporation energy and/or radiofrequency energy, or other types of energy, and to record EGM and/or MAP signals.

The medical device 12 may be a treatment and mapping device, and may generally be configured as shown and described in FIG. 1. However, although the device 12 may include a treatment element 32 that includes a plurality of electrodes 38/66 that are in communication with the pulsed electric field generator 14, the treatment element 32 may have a configuration that is the same or different than that shown in FIG. 1. For example, the treatment element 32 may include a flexible carrier element 36 bearing the electrodes 38/66, and the carrier element 36 may be transitionable between a linear configuration and an expanded configuration in which the carrier element 36 has an arcuate or substantially arcuate configuration (as shown in FIG. 1). On the other hand, the treatment element 32 may be a focal catheter including a linear array of electrodes 38/66. The treatment element 32 shown in FIGS. 27 and 28 may be a linear array of electrodes 38/66 along a length of the distal portion 28 of a focal catheter; however, it will be understood that the treatment element shown in FIGS. 27-39 may instead be a portion or segment of a treatment element such as that shown in FIG. 1, or any of a variety of treatment elements having a multi-electrode configuration. The concave electrodes 66 shown and described in FIGS. 27, 28, and 30 may be located along a length of a linear catheter or along a length of a carrier element having a linear, looped, or other configuration. The concave electrodes 66' shown and described in FIGS. 31-34 are located at a distalmost tip of an elongate body 22 or carrier element 32.

Figure 27:
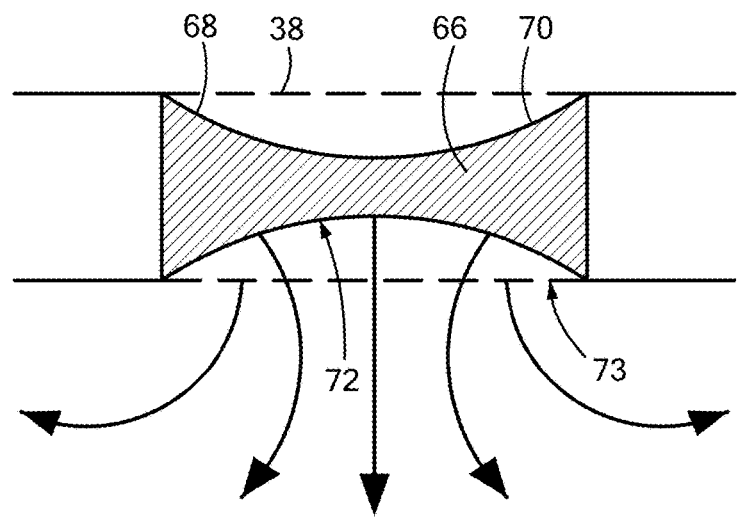
FIG. 27 shows a comparison between a currently known ring electrode and a first embodiment of a concave electrode.
Figure 28:
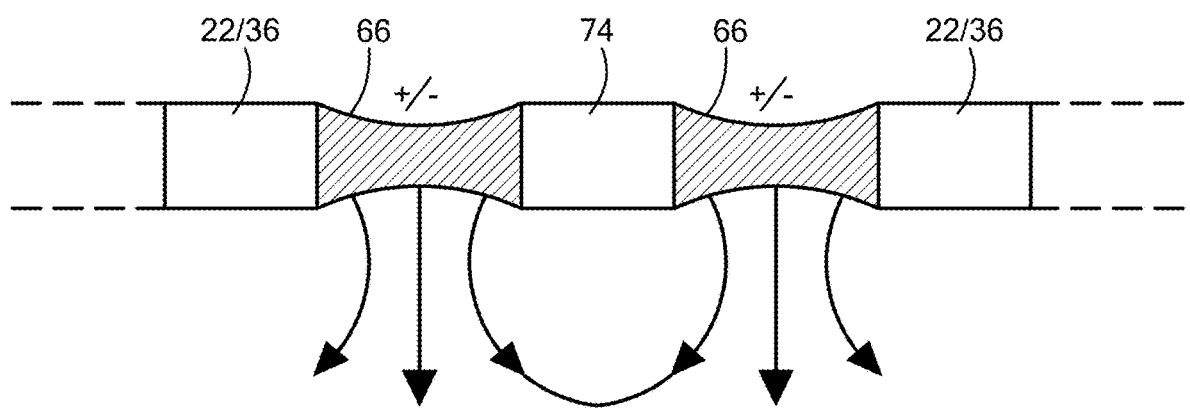
FIG. 28 shows a portion of a treatment element including two or more concave electrodes.
Figure 29:
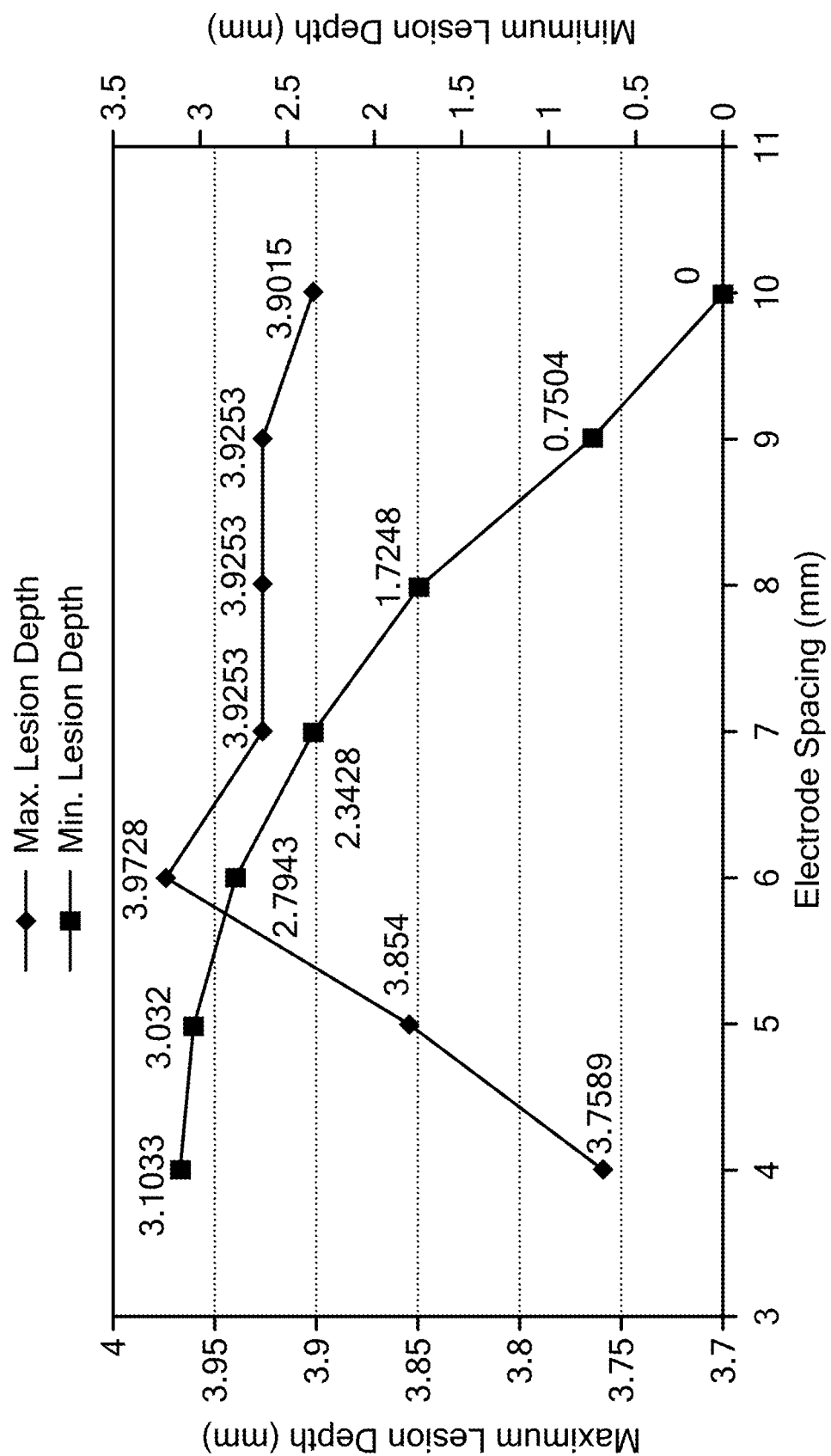
FIG. 29 shows a graph illustrating an exemplary relationship between electrode spacing and lesion depth.
Figure 30:
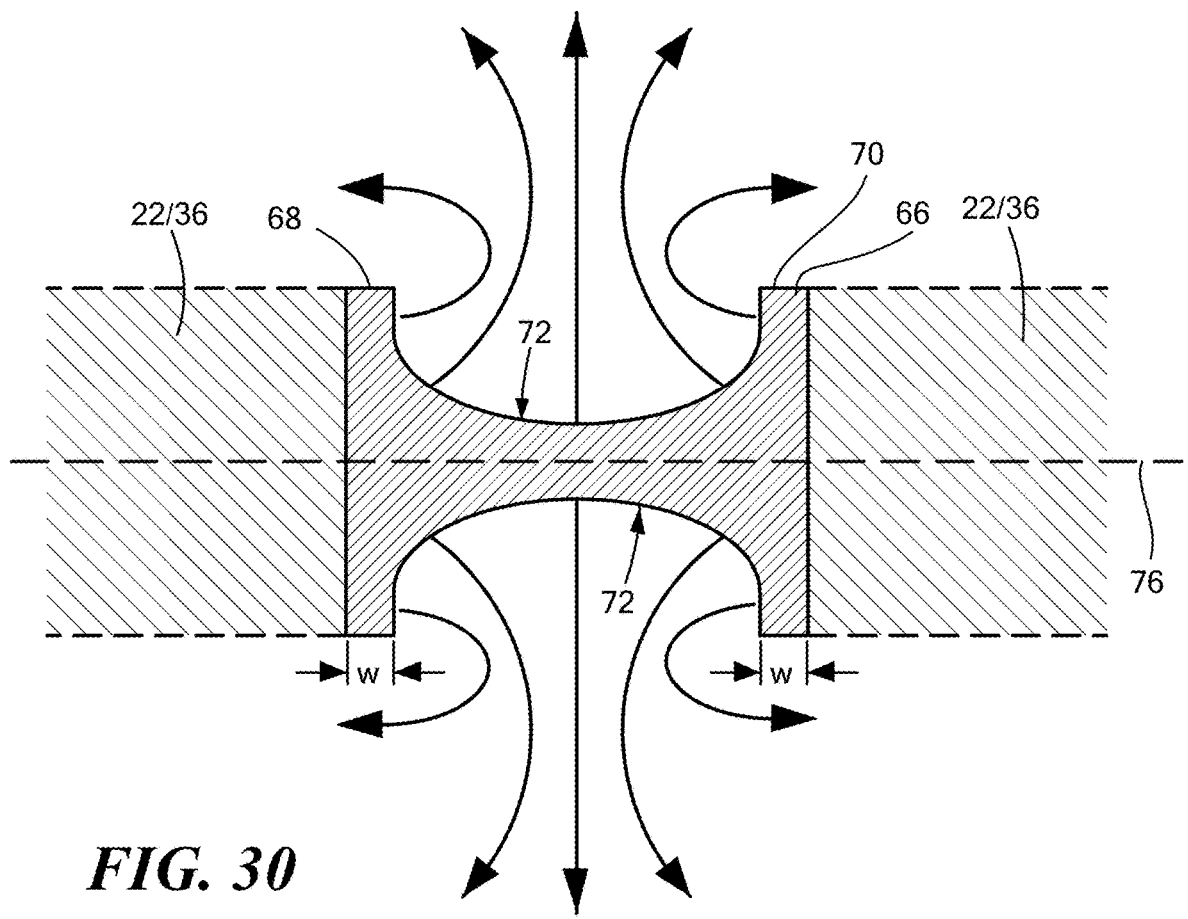
FIG. 30 shows a second embodiment of a concave electrode.

Referring now to FIG. 27, a comparison between a currently known ring electrode and a first embodiment of a concave electrode is shown. The currently known electrode 38 may be any conventional electrode, such as a ring electrode (for example, as shown in dashed lines in FIG. 27) composed of an electrically conductive material and having a cylindrical shape with an at least substantially circular cross section and at least substantially straight parallel sides. Although the concave electrode 66 may be considered a "ring" electrode in that it may circumscribes or extend all the way around a circumference of the device elongate body 22 or carrier element 36, at least a portion of the electrode 66 may be concave (that is, curving in toward a midpoint within the elongate body 22 or carrier element 36), as shown in FIGS. 27, 28, and 30. As a non-limiting example, the electrode 66 be shaped as a concave cylinder having a first end 68 and a second end 70, and a first diameter at a point between the first end 68 and second end 70 that is less than a second diameter at either end 68, 70. The first diameter may be a minimum diameter and the second diameter may be a maximum diameter, with gradually increasing diameters from the first diameter to either of the first 68 or second 70 diameters.

Electric fields are projected from a conductive surface perpendicular to that surface. Using this principle the electric field may be concentrated for pulsed electric field energy (and/or radiofrequency energy) delivery by using a concave electrode 66 as compared to using a currently known electrode 38. Electric fields are depicted in the figures using arrows. As shown in FIG. 27, the curved surface 72 of the concave electrode may cause the electric fields to concentrate within tissue proximate the electrode and may drive the electric fields deeper into the tissue as compared to the flat or straight surface 73 of the currently known electrode 38. Additionally, when a concave electrode 66 is pressed against tissue, the tissue may extend into the concavity of the electrode 66, thereby increasing the amount of tissue exposed to the energy delivery, which may contribute to deeper lesion formation.

Referring to FIG. 28, a portion of a treatment element is shown that includes two or more concave electrodes. As a non-limiting example, the electrodes 66 may be as shown and described in FIG. 27 with an electrically insulated segment 74 between each pair of adjacent electrodes 66. Additionally, each electrode 66 may be located between two adjacent insulated segments 74. The electrode ends 68, 70 may be approximately flush with the outer diameter of the elongate body 22 or the carrier element 26, or one or both ends 68, 70 may extend or protrude beyond the outer diameter of the elongate body 22 or carrier element 26.

Two electrodes are shown in FIG. 28 as being either positive or negative polarity ("+/−"). Adjacent electrodes 66 may have the same or opposite polarities (for example, if bipolar energy is delivered), and bipolar delivery is shown in FIG. 28. So, if one electrode is connected to the negative polarity of the generator 14, the other electrode will be connected to the positive polarity of the generator 14. As discussed above, the concave shape of the electrodes 66 may concentrate the electric fields and may drive the electric fields deeper into the tissue.

The electrodes may be separated by any distance; however, it has been found that an optimal distance between electrodes may be between approximately 5 mm and approximately 6 mm. That is, at this spacing, bipolar energy delivery may create lesions to a maximum depth within the tissue. A trend between electrode spacing, maximum lesion depth, and minimum lesion depth is shown in the graph in FIG. 29.

Now referring to FIG. 30, a second embodiment of a concave electrode is shown. The concave electrode 66 shown in FIG. 30 may be generally similar to the first embodiment of the concave electrode shown in FIGS. 27 and 28, except that each end 68, 70 may have a width W over which the diameter of the electrode is continuous. Further, the concavity of the electrode 66 may be more arched than that of the first embodiment, and therefore may deliver electric fields that are directed parallel or substantially parallel to the longitudinal axis 76 of the electrode. Electric fields flowing in directions along or approximate to the longitudinal axis 76 may impinge upon electric fields being directed at angles to the longitudinal axis 76, further concentrating the energy delivery and driving the energy deeper into the tissue.

Referring now to FIGS. 31-34, concave tip electrodes are shown. Each concave tip electrode 66' may be located within, at, or proximate a distalmost tip or edge 80 of an elongate body 22 or carrier element 32. Further, the concave tip electrode 66' may be the only electrode in the treatment element 32 or may be included in addition to one or more concave 38 or other electrodes located along the length of the elongate body 22 or carrier element 32.

Figure 31:
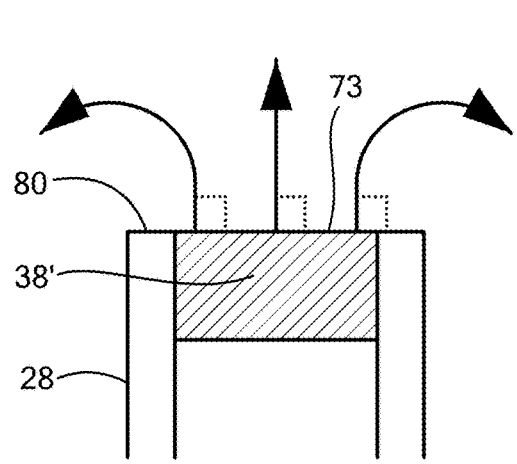
FIG. 31 shows electric field distribution from a currently known tip electrode having a flat distal face.
Figure 32:
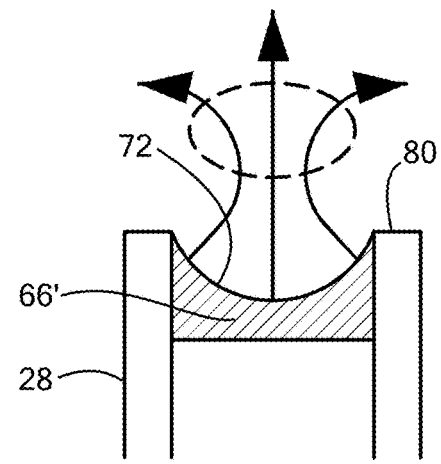
FIG. 32 shows electric field distribution from a tip electrode having a concave distal face.

FIG. 31 shows electric field distribution from currently known distal tip electrode 38' having a flat surface 73. As discussed above, electric fields are projected from a conductive surface perpendicular to that surface, and energy will be transmitted from the currently known distal tip electrode 38' as shown and described in FIG. 27. FIG. 32 shows electrical field distribution from a concave distal tip electrode 66'. As discussed above and shown in FIG. 32, the electric field may be concentrated for pulsed electric field energy (and/or radiofrequency energy) delivery by using the concave distal tip electrode 66' as compared to using a currently known distal tip electrode 38'.

Figure 33:
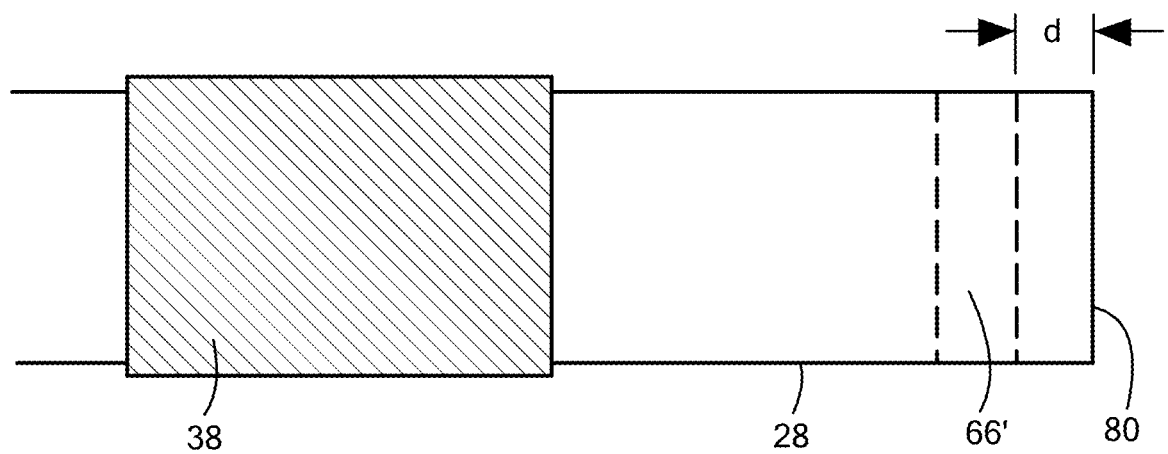
FIG. 33 shows a side view of a distal portion of a medical device having a concave tip electrode.
Figure 34:
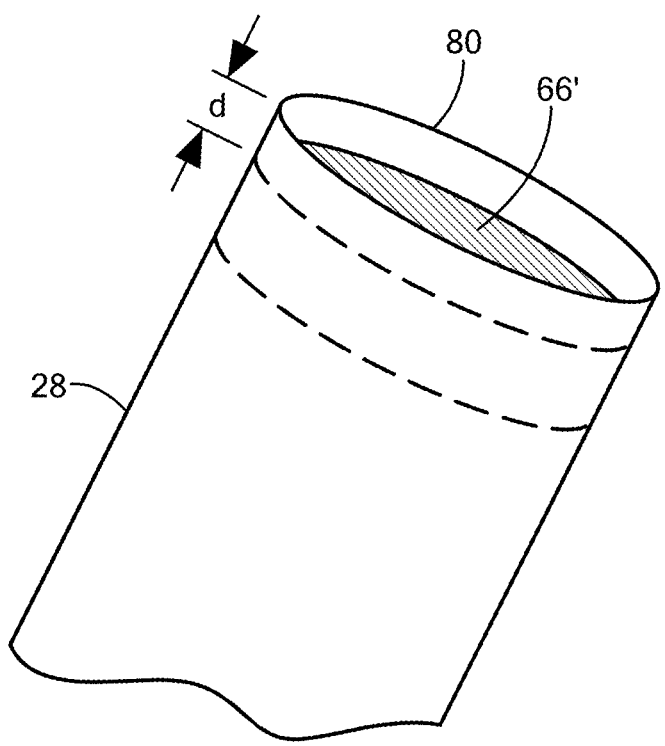
FIG. 34 shows a perspective view of the distal portion of the medical device having a concave tip electrode of FIG. 32.

Referring now to FIGS. 33 and 34, a side view and a perspective view of a distal portion of a medical device having a concave tip electrode are shown. As shown in FIG. 33, the device 12 may also include one or more other electrodes along the length of the elongate body 22 (or carrier element 36), which electrodes may optionally be concave electrodes. In the non-limiting configuration shown in FIG. 33, the electrodes may be currently known ring electrodes 38. The concave distal tip electrode 66' may have a substantially circular cross-sectional shape, or any other cross-sectional shape, that matches a cross-sectional shape of the elongate body 22 (or carrier element 36) distal end. As such, the concave distal tip electrode 66' may have a hemispherical or bowl-shaped configuration. Further, the concave distal tip electrode 66' may optionally be recessed within the elongate body 22 or carrier element 36 by a distance d from the distalmost tip or edge 80 of the elongate body 22 or carrier element 36. This recessed location may allow the electrode 66' to be protected by the insulated elongate body 22 or carrier element 36, except for the exposed surface 72. The distal tip of the device 12 may then be placed in contact with the target tissue to deliver energy in a concentrated manner. When the concave distal tip electrode 66' is pressed against tissue, the tissue may extend into the concavity of the electrode 66', thereby increasing the amount of tissue exposed to the energy delivery, which may contribute to deeper lesion formation.

Referring now to FIGS. 35-40, a various configurations of a treatment element including a plurality of electrodes and at least one insulated, protuberant segment are shown. The electrodes may be currently known electrodes 38, such as ring electrodes (as shown in FIGS. 35 and 37-40), or may be concave electrodes 38 as shown and described herein. The electrodes 38 may alternate with one or more protuberant segments 84 of the elongate body 22 or carrier element 36 that are insulated. That is, the protuberant segments may extend farther outward from the longitudinal axis of, for example, the elongate body 22, than the neighboring electrodes 38. When the protuberant segments 84 are pressed against the tissue, they may compressed the tissue and allow for deeper lesion formation by increasing the tissue area exposed to energy delivery.

Figure 35:
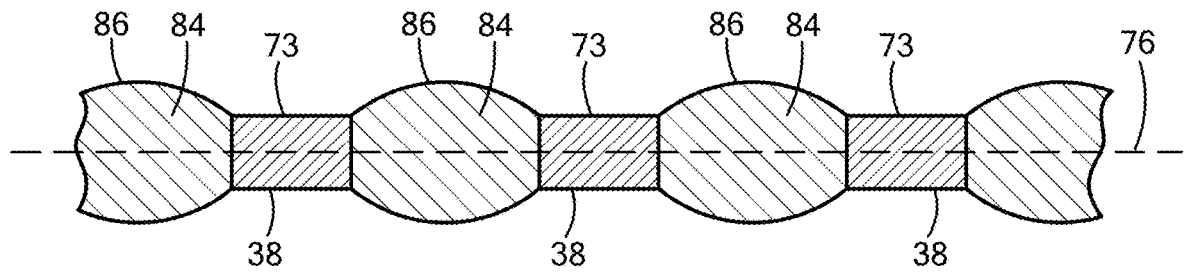
FIG. 35 shows a portion of a treatment element including a plurality of electrodes alternating with a plurality of a first embodiment of insulated, protuberant segments.
Figure 36:
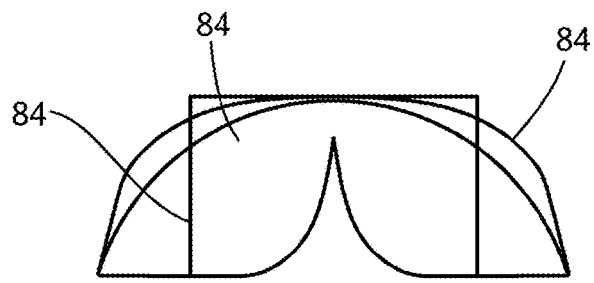
FIG. 36 shows a comparison of a plurality of profiles of insulated, protuberant segments.

Referring now to FIG. 35, the treatment element 32 may include a plurality of electrodes 38, such as ring electrodes, and a plurality of protuberant segments 84 alternating with the electrodes. As shown, the surfaces 86 of the protuberant segments 84, at least at the portion of each segment 84 having the widest diameter, may extend farther from the electrode longitudinal axis 76 than the surface 73 of the electrodes 38. Although the first embodiment of segment 84 is shown in FIG. 35 as having a rounded surface 73, it will be understood that the protrusions 84 may have any surface configuration or profile that is a protrusion as compared to the electrode surfaces 73. For example, a variety of profiles are shown in FIG. 36 for comparison. As a non-limiting example, the surface 73 may be squared, rounded, triangular, or the like.

Figure 37:
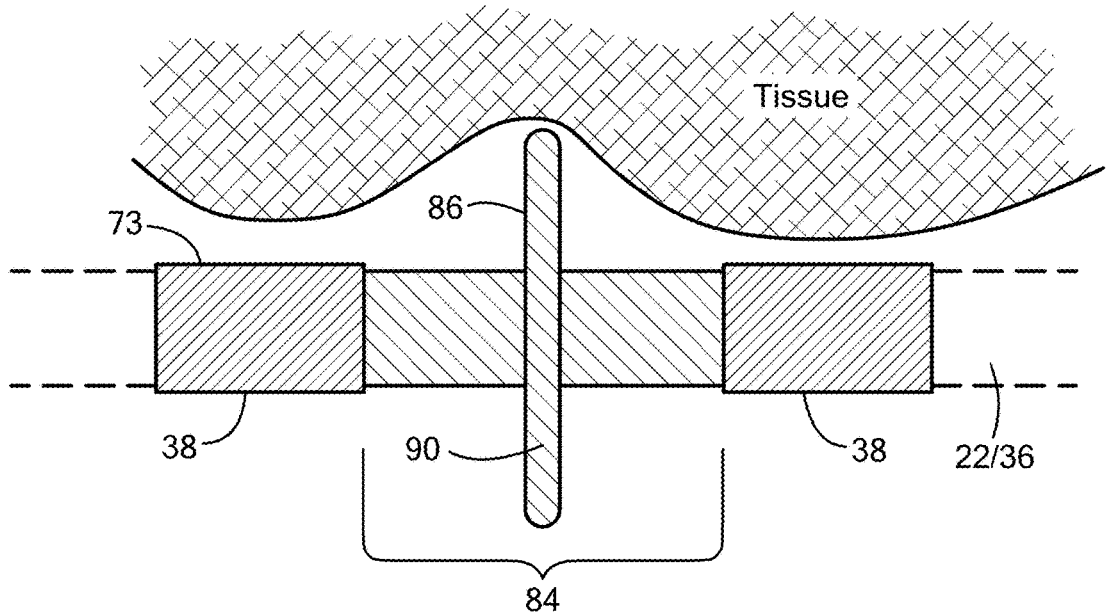
FIG. 37 shows a portion of a treatment element including a plurality of a first embodiment of electrodes and at least one of a second embodiment of an insulated, protuberant segment.
Figure 38:
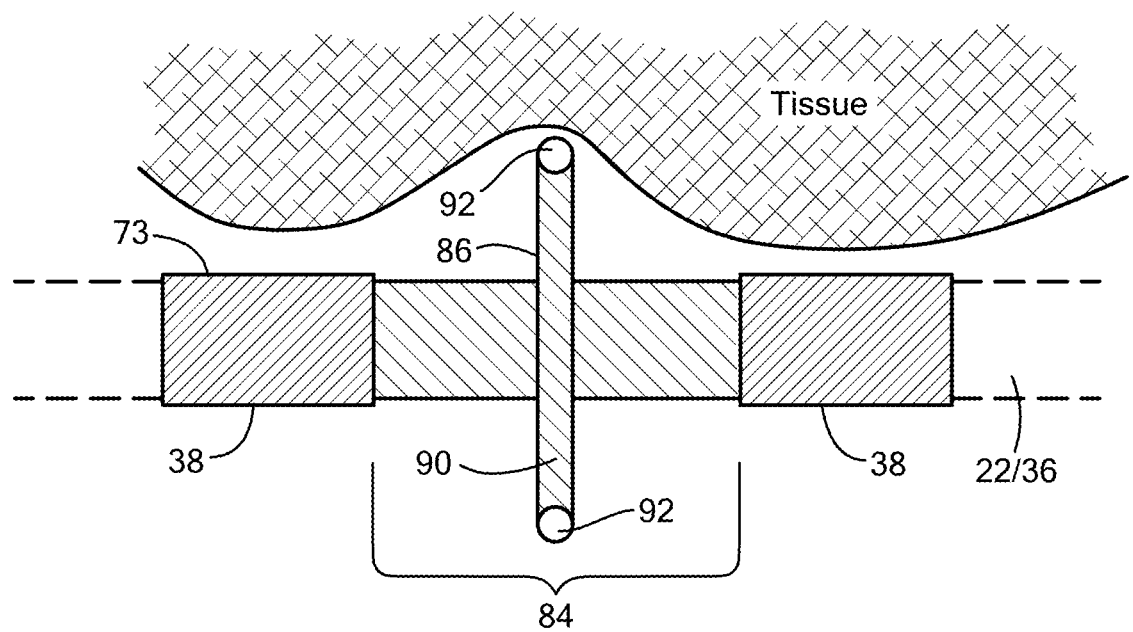
FIG. 38 shows a portion of a treatment element including a plurality of a second embodiment of electrodes and at least one of the second embodiment of an insulated, protuberant segment.

Referring now to FIGS. 37 and 38, a treatment element is shown that includes a plurality of a second embodiment of protuberant segments alternating with a plurality of electrodes is shown. Each segment 84 may have a first portion that has a diameter that is substantially the same as that of the elongate body 22 and/or the carrier element 36 and a second portion that includes the protrusion 90. The protrusion 90 may be a ring that extends around at least a portion of the circumference of the elongate body 22 and/or the carrier element 36. In the embodiment shown in FIG. 33, the protrusion 90 may be a ring that extends around at least substantially an entirety of the circumference of the elongate body 22 and/or the carrier element 36. Alternatively, protrusion 90 may include one or more cone-shaped protrusions that are radially located at least partially around the circumference of the cylindrical portion. However, these configurations are merely exemplary and, as discussed above, the protrusions may have any suitable configuration. Further, each electrode 38 may have a length along the electrode longitudinal axis that is the same as or greater than a width of the protrusion immediately adjacent or proximate to the electrode 38 along the same axis. The electrode configuration shown in FIGS. 37 and 38 may allow for greater heat dissipation from the electrodes 38 during energy delivery.

Referring specifically to FIG. 38, each segment 84 may include one or more mapping electrodes 92 for recording signals from tissue, such as monophasic action potentials (MAPs). Additionally or alternatively, each segment 84 may include one or more sensors, such as temperature and/or pressure sensors. Including mapping electrodes 92 on the protrusions 84 may enhance mapping signal quality when the tissue is compressed by the protrusion.

Figure 39:
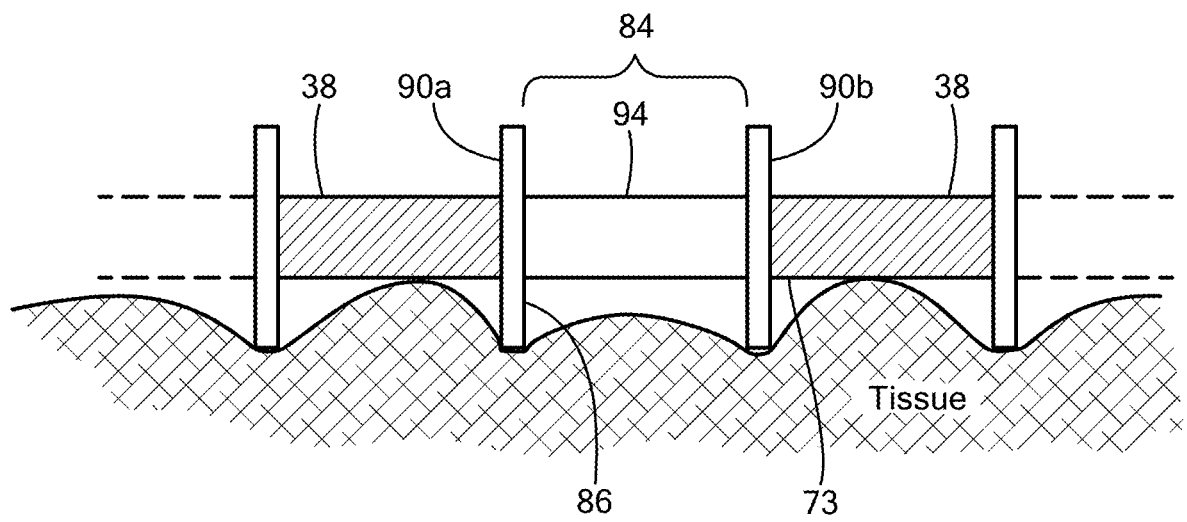
FIG. 39 shows a portion of a treatment element including a plurality of electrodes and at least one of a third embodiment of an insulated, protuberant segment.

Referring now to FIG. 39, a portion of a treatment element including a plurality of electrodes and at least one of a third embodiment of an insulated, circumferential protuberant segment is shown. Each segment 84 may include a first protrusion 90a at a first end of the segment, a second protrusion 90b at a second end of the segment opposite the first end, and a length 94 between the first 90a and second 90b protrusions. Each of the first 90a and second 90b protrusions may be immediately adjacent the nearest electrode 38. As a non-limiting example, each of the first 90a and second 90b protrusions may be disk shaped and may encircle the entire circumference of the length 94. As shown in FIG. 39, each protrusion 90a, 90b may have a diameter that is greater than the greatest diameter of the length 94. The length of the segment 84 may provide the desired spacing between adjacent electrodes 38, whereas the protrusions 90a, 90b immediately adjacent the electrodes 38 may cause the tissue to extend into the space between the protrusions 90a, 90b, and therefore closer to the electrode 38, when the treatment element 32 is pressed against the tissue. This may increase the amount of tissue exposed to the energy delivery, which may contribute to deeper lesion formation.

Figure 40:
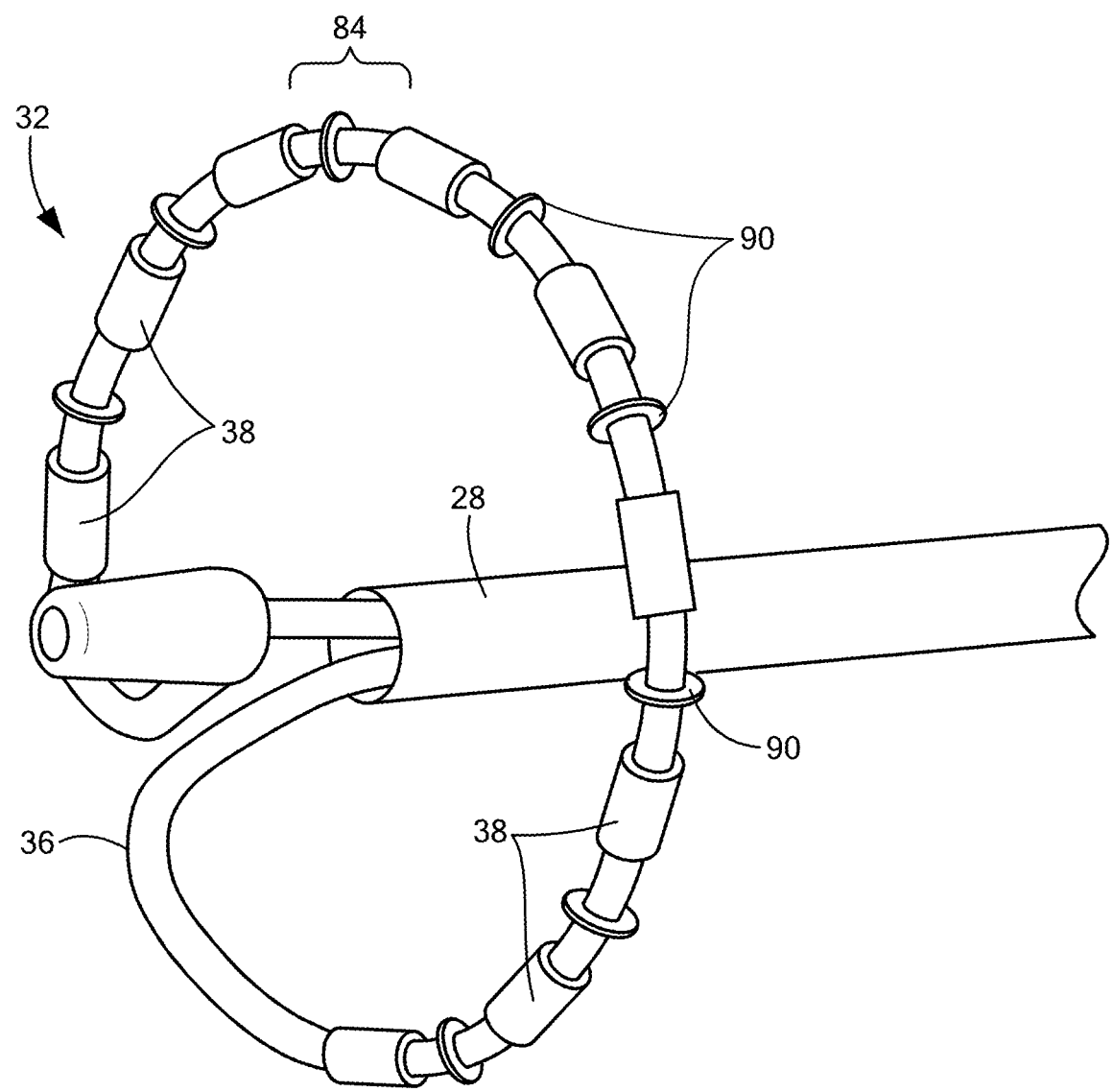
FIG. 40 shows a treatment element including a plurality of electrodes and a plurality of a fourth embodiment of insulated, protuberant segments.

Referring now to FIG. 40, an exemplary treatment element is shown that includes a plurality of electrodes and a plurality of a fourth embodiment of a circumferential protuberant segments is shown. The treatment element 32 may include a carrier element 36 that is transitionable between a linear configuration and an expanded configuration in which the carrier element 36 has an arcuate or substantially arcuate configuration, for example, as shown in FIGS. 1-25. The carrier element 36 may include a plurality of electrodes 38 and a plurality of protuberant segments 84. The electrodes 38 may be currently known electrodes (that is, not concave), as shown in FIG. 39, or concave electrodes 66 as shown and described herein. A plurality of insulated protuberant segments 84 may be mounted on or affixed to the carrier element 36 between the electrodes 38, or the carrier element 36 may define the plurality of protuberant segments 84, each protuberant segment 84 including at least one protrusion 90. That is, the carrier element 36 may be insulated and may be manufactured to include a plurality of protrusions 90 between the electrodes 38. In the exemplary configuration of FIG. 39, each protuberant segment 84 may include a ring-shaped protrusion 90 that extends around at least substantially the entirety of the circumference of the carrier element 36. Alternatively, each protuberant segment 84 may include a ring-shaped or ridge-shaped protrusion 90 that extends around at least a portion of the circumference of the carrier element 36. For example, each segment 84 may include a protrusion on only that portion of the segment 84 that is exposed to tissue when the carrier element 36 is in the expanded configuration.

Referring now to FIGS. 41-44, a distal portion of a medical device having a plurality of active electrodes and a plurality of neutral electrodes is shown, as well as exemplary ablation patterns depending on whether the neutral electrodes are electrically connected to each other. Like the treatment element 32 shown in FIGS. 1-25, the treatment element 32 of FIGS. 41 and 42, when used with the system 10 described herein, provides the ability to control the delivery of ablation energy, including the depth and placement of lesions in tissue. The device shown in FIGS. 41 and 42 may be used with the system shown in FIG. 1 and described above to deliver pulsed electric field electroporation energy and/or radiofrequency energy.

The medical device 12 may be a treatment and mapping device, and may generally be configured as shown and described in FIG. 1. However, although the device 12 may include a treatment element 32 that includes a plurality of electrodes 38 that are in communication with the pulsed electric field generator 14, the treatment element 32 may have a configuration that is the same or different than that shown in FIG. 1. For example, the treatment element 32 may include a flexible carrier element 36 bearing the electrodes 38, and the carrier element 36 may be transitionable between a linear configuration and an expanded configuration in which the carrier element 36 has an arcuate or substantially arcuate configuration (as shown in FIG. 1). On the other hand, the treatment element 32 may be a focal catheter including a linear array of electrodes 38. The treatment element 32 shown in FIGS. 27 and 28 may be a linear array of electrodes 38 on the distal portion 28 of a focal catheter; however, it will be understood that the treatment element shown in FIGS. 41 and 42 may instead be a portion of a treatment element such as that shown in FIG. 1, or any of a variety of treatment elements having a multi-electrode configuration.

Figure 41:
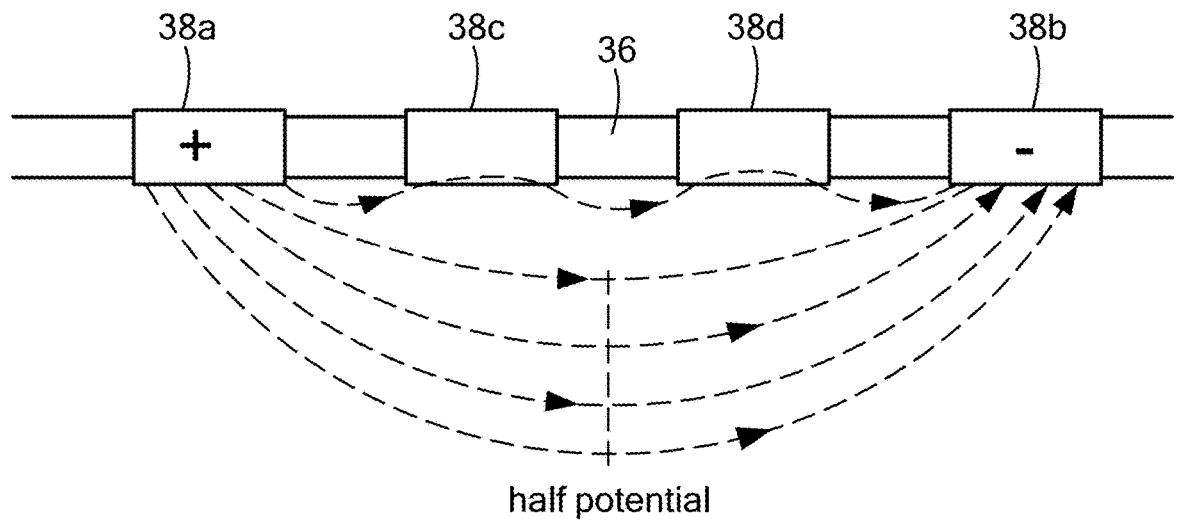
FIG. 41 shows a distal portion of a medical device having a plurality of active electrodes and a plurality of neutral electrodes, the active electrodes delivering ablation energy and the neutral electrodes being electrically disconnected from each other.

Referring now to FIG. 41, a treatment element 32 (or portion of a treatment element) is shown that includes a first active electrode 38*a*, a second active electrode 38*b*, a first neutral electrode 38*c*, and a second neutral electrode 38*d*. Although not shown, the device may include additional active and/or neutral electrodes. The first 38*a* and second 38*b* active electrodes may have opposite polarities, with the first active electrode 38*a* being connected to a first polarity and the second active electrode 38*b* being connected to a second polarity. For example, the first active electrode 38*a* may be connected to the positive polarity of the generator 14 and the second active electrode 38*b* may be connected to the negative polarity of the generator 14. The first 38*c* and second 38*d* neutral electrodes may be located between the first 38*a* and second 38*b* active electrodes.

The neutral electrodes 38*c*, 38*d* may be insulated or isolated from a ground reference, therefore acting as a path for the current instead of a source or a sink. When energy is delivered from the active electrodes 38*a*, 38*b*, the energy may be delivered in bipolar mode due to the polarities of the active electrodes 38*a*, 38*b*. Therefore, current flows between the active electrodes 38*a*, 38*b* through the tissue with which the electrodes are in contact. The exact path in which the current flows is the path of least electrical resistance. As the neutral electrodes 38*c*, 38*d* are electrically conductive (even though not delivering energy to the tissue) and have a lower resistance than tissue, at least some of the current between the active electrodes 38*a*, 38*b* may flow between the active electrodes 38*a*, 38*b* and the neutral electrodes 38*c*, 38*d*, and between the neutral electrodes 38*c*, 38*d* themselves (as shown in FIG. 41). A lesion 96 is most likely to form in the tissue where the current flow is the most concentrated. As shown in FIG. 40, the half potential may be approximately halfway between the active electrodes 38*a*, 38*b*, which means the current is the most concentrated closer to the active electrodes 38*a*, 38*b*. This delivery pattern may produce the two tissue lesion 96 shown in FIG. 43, with one lesion being produced beneath or proximate the first active electrode 38*a* and the other lesion being produced beneath or proximate the second active electrode 38*b*. As a small amount of current flows through the neutral electrodes 38*c*, 38*d* as the path of least resistance, one or more small lesions may be formed beneath or proximate each of the neutral electrodes 38*c*, 38*d*.

Figure 42:
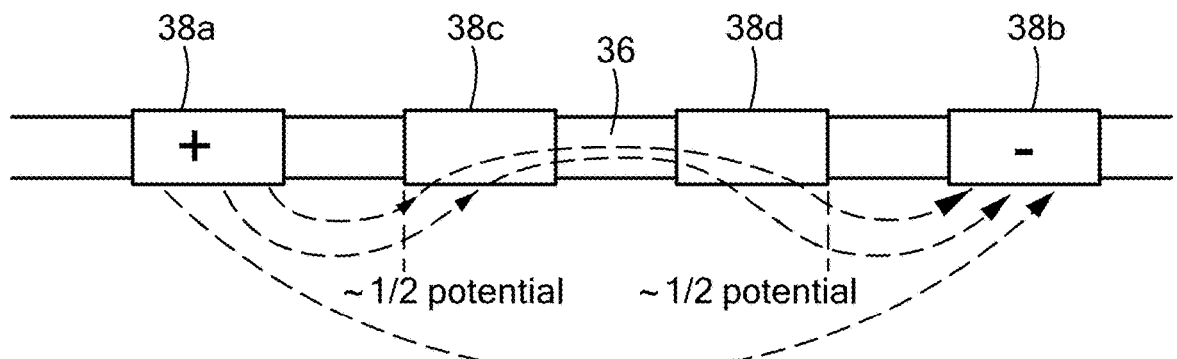
FIG. 42 shows the distal portion of the medical device of FIG. 41, the active electrodes delivering ablation energy and the neutral electrodes being electrically connected to each other.
Figure 43:
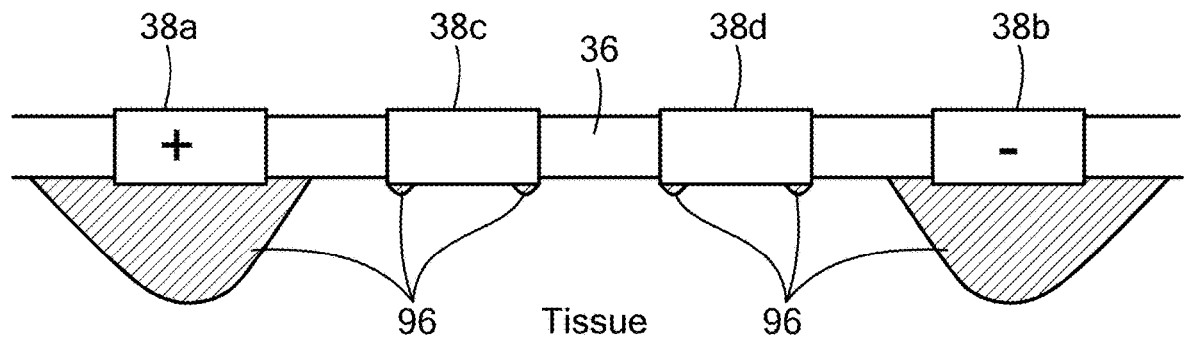
FIG. 43 shows an exemplary lesion formation in tissue by the ablation energy being delivered to the tissue as shown in FIG. 41.
Figure 44:
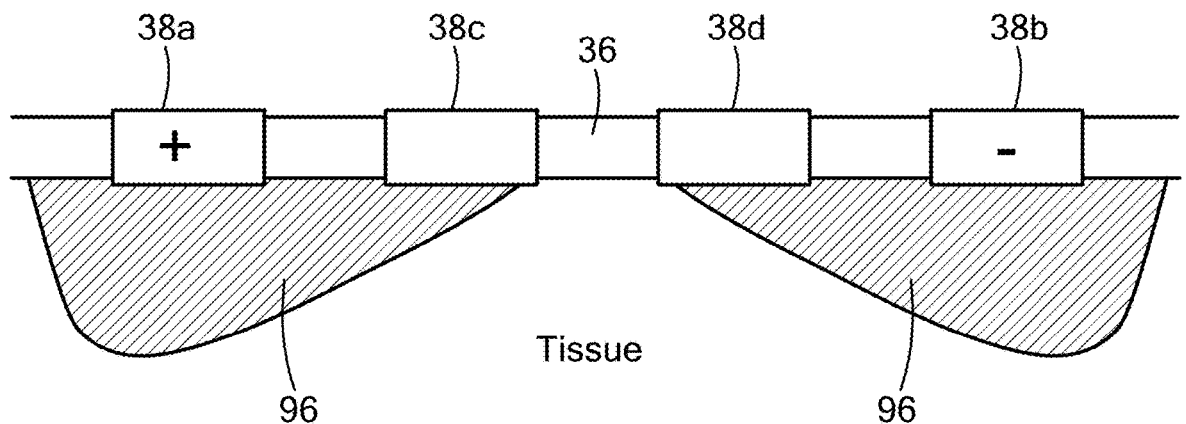
FIG. 44 shows an exemplary ablation pattern created in tissue by the ablation energy being delivered to the tissue as shown in FIG. 42.

However, when the neutral electrodes 38*c*, 38*d* are electrically connected to each other (as shown in FIG. 42), the low resistance path through the neutral electrodes 38*c*, 38*d* spans a greater distance between the active electrodes 38*a*, 38*b*, as the current is even more likely to flow through the lower resistance metal than tissue, blood, or the like than when the neutral electrodes 38*c*, 38*d* are electrically disconnected from each other. This delivery pattern may therefore concentrate more current and produce larger tissue lesions in the areas of greatest concentration. The connection between the neutral electrodes 38*c*, 38*d* may be made within the elongate body 22 and/or the carrier element 36, or may be made by the device electrode distribution system 16 or other relays or switches. As shown in FIG. 42, a half potential may be between the first active electrodes 38*a* and the first neutral electrode 38*c*, at a location closer to the first neutral electrode 38*c*, and another half potential may be between the second active electrode 38*b* and the second neutral electrode 38*d*, at a location closer to the second neutral electrode 38*d*. This delivery pattern may produce the two tissue lesion shown in FIG. 44, with one lesion being produced between the first active electrode 38*a* and the first neutral electrode 38*c* and the other lesion being produced between the second active electrode 38*b* and the second neutral electrode 38*d*. Further, the lesions may be slightly deeper proximate the active electrodes 38*a*, 38*b*.

By selectively connecting or disconnecting the neutral electrodes 38*c*, 38*d* from each other, the user may modify energy delivery by concentrating and/or redirecting the energy. The ability to more precisely control energy delivery may enhance patient safety by allowing the user to avoid delivering energy to sensitive areas. For example, if a nerve or other sensitive anatomical feature were located between the neutral electrodes, the neutral electrodes could be electrically connected to each other to minimize the amount of energy delivered between the neutral electrodes and also may concentrate energy delivery to the tissue proximate the active electrodes. Further, the system may allow for the creation of deeper and more specific ablation zones. It will be understood that the lesions shown in the figures are for illustration only, and energy delivery as described herein may not produce lesions with the same size or configuration. The lesions that are actually created may depend on a variety of factors, such as the applied voltage, total current, and/or other waveform parameters.

As will be appreciated by one of skill in the art, certain concepts described herein may be embodied as a method, data processing system, and/or computer program product. Accordingly, these concepts described herein may take the form of an entirely hardware embodiment, an entirely software embodiment or an embodiment combining software and hardware aspects. Furthermore, the disclosure may take the form of a computer program product on a tangible computer usable storage medium having computer program code embodied in the medium that can be executed by a computer. Any suitable tangible computer readable medium may be utilized including hard disks, CD-ROMs, electronic storage devices, optical storage devices, or magnetic storage devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for the delivery of ablation energy, the system comprising:
a medical device configured to ablate and map tissue, the medical device including:
an elongate body defining a longitudinal axis;
a treatment element having a carrier element, the carrier element having a plurality of electrodes;
each electrode in the plurality of electrodes having a concave cylindrical shape and including:
a first end;
a second end opposite the first end, the first end and the second end each having a first diameter;
a single concavity defined entirely between the first end and the second end; and
a diameter at any given point between the first end and the second end being smaller than the first diameter;
the carrier element being transitionable between a substantially linear configuration and an expanded configuration, each of the plurality of electrodes in the expanded configuration being coplanar in a plane that is substantially orthogonal to the longitudinal axis of the elongate body, the plurality of electrodes being arranged in a plurality of pairs of a first electrode and a second electrode, the first electrode and the second electrode of each electrode pair being separated by a first distance, each electrode pair being separated by a second distance greater than the first distance;
an electrically insulated segment disposed between the first electrode and the second electrode of each electrode pair and having a length less than the first electrode and the second electrode;
a mapping signal recording system; and
an energy generator in communication with the treatment element, the energy generator being configured to, when the energy generator is transmitting energy:
electrically connect each of the plurality of electrodes to the energy generator;
electrically connect the first electrode and the second electrode of each of the plurality of electrode pairs to each other such that every other electrode pair has the same polarity;
transmit ablation energy to the plurality of electrodes such that adjacent electrode pairs deliver bipolar energy; and
when the energy generator is not transmitting energy, the energy generator being configured to:
electrically disconnect the first electrode and the second electrode of each of the plurality of electrode pairs from each other;
connect each of the plurality of electrodes to the mapping signal recording system; and
record intracardiac electrogram signals from each of the plurality of electrodes with the mapping signal recording system while the first electrode and the second electrode of each of the plurality of electrode pairs is electrically disconnected from each other.

2. The system of claim 1, wherein the ablation energy is pulsed electric field ablation energy.

3. The system of claim 1, wherein the first distance is between approximately 1.0 mm and approximately 2.0 mm.

4. The system of claim 1, wherein the second distance is between approximately 2.0 mm and 6.0 mm.

5. The system of claim 1, wherein the system further includes a navigation system, the energy generator being further configured to, when the energy generator is not transmitting ablation energy:
electrically disconnect the first electrode and the second electrode of each of the plurality of electrode pairs from each other;
connect each of the plurality of electrodes to the navigation system; and
at least one of transmit navigation energy to and receive navigation energy from each of the plurality of electrodes.

6. The system of claim 1, wherein the system further includes a positioning and navigation system, the energy generator being further configured to, when the energy generator is not transmitting ablation energy:
electrically disconnect the first electrode and the second electrode of each of the plurality of electrode pairs from each other;
connect each of the plurality of electrodes to the mapping signal recording system and to the positioning and navigation system;
transmit cardiac electrical activity measurements to the mapping signal recording system; and
transmit positioning and navigation signals to or from each of the plurality of electrodes.

7. The system of claim 1, wherein the plurality of electrodes is a first plurality of electrodes, the treatment element further having a second plurality of electrodes, each electrode of the second plurality of electrodes being located between adjacent electrode pairs of the first plurality of electrodes.

8. The system of claim 7, wherein the second plurality of electrodes is electrically disconnected from the energy generator and the mapping signal recording system when the energy generator transmits ablation energy.

9. The system of claim 1, wherein the treatment element has a substantially circular shape when in the expanded configuration.

10. The system of claim 1, further comprising an electrode distribution system, the electrode distribution system being configured to monitor a total amount of energy delivered by each of the plurality of electrodes.

11. The system of claim 1, wherein each electrode in the plurality of electrodes includes a midpoint defined halfway between the first end and the second end, the midpoint having a second diameter smaller than the first diameter.

* * * * *